(12) United States Patent
Gil et al.

(10) Patent No.: US 9,037,205 B2
(45) Date of Patent: May 19, 2015

(54) IMPLANTABLE OPTICAL GLUCOSE SENSING

(75) Inventors: Tamir Gil, Givat Haim (IL); Yossi Gross, Mazor (IL); Orly Grinberg, Modi'in (IL); Itamar Weisman, Yad Rambam (IL); Tehila Hyman, Modi'in (IL); Boaz Hyman, Modi'in (IL)

(73) Assignee: GLUSENSE, LTD, Lod (IL)

( * ) Notice: Subject to any disclaimer, the term of this patent is extended or adjusted under 35 U.S.C. 154(b) by 533 days.

(21) Appl. No.: 13/173,831

(22) Filed: Jun. 30, 2011

(65) Prior Publication Data

US 2013/0006069 A1    Jan. 3, 2013

(51) Int. Cl.
*A61B 5/1455*    (2006.01)
*A61B 5/1459*    (2006.01)
*A61B 5/145*    (2006.01)
*A61B 5/00*    (2006.01)

(52) U.S. Cl.
CPC ............ *A61B 5/1459* (2013.01); *A61B 5/0071* (2013.01); *A61B 5/14532* (2013.01)

(58) Field of Classification Search
USPC ................................................ 600/309–344
See application file for complete search history.

(56) References Cited

U.S. PATENT DOCUMENTS

| | | | |
|---|---|---|---|
| 3,774,243 A | 11/1973 | Ng et al. | |
| 3,837,339 A | 9/1974 | Aisenberg et al. | |
| 3,837,922 A | 9/1974 | Ng et al. | |
| 3,861,397 A | 1/1975 | Rao et al. | |
| 4,140,963 A | 2/1979 | Rao et al. | |
| 4,344,438 A * | 8/1982 | Schultz | 600/341 |
| 4,352,883 A | 10/1982 | Lim | |
| 4,402,694 A | 9/1983 | Ash et al. | |
| 4,578,323 A | 3/1986 | Hertl et al. | |
| 4,721,677 A | 1/1988 | Clark, Jr. | |
| 4,953,976 A | 9/1990 | Adler-Golden et al. | |
| 4,981,779 A | 1/1991 | Wagner | |
| 5,001,054 A | 3/1991 | Wagner | |
| 5,011,472 A | 4/1991 | Aebischer et al. | |
| 5,089,697 A | 2/1992 | Prohaska | |
| 5,101,814 A | 4/1992 | Palti | |
| 5,116,494 A | 5/1992 | Chick et al. | |
| 5,143,066 A | 9/1992 | Komives et al. | |
| 5,209,231 A | 5/1993 | Cote et al. | |

(Continued)

FOREIGN PATENT DOCUMENTS

WO    90/15526    12/1990
WO    91/01680    2/1991

(Continued)

OTHER PUBLICATIONS

An Office Action dated Jan. 10, 2013, which issued during the prosecution of U.S. Appl. No. 12/225,749.

(Continued)

*Primary Examiner* — Eric Winakur
*Assistant Examiner* — Marjan Fardanesh
(74) *Attorney, Agent, or Firm* — Symbus Law Group, LLC; Clifford D. Hyra

(57) ABSTRACT

Apparatus is provided for detecting an analyte, configured to be implanted in a body of a subject. The apparatus includes an optical fiber having a distal portion and also a membrane permeable to the analyte. The membrane is coupled to the distal portion of the fiber and surrounding a sampling region at least in part, by being fitted over the distal portion of the fiber. Other embodiments are also described.

23 Claims, 9 Drawing Sheets

(56) References Cited

U.S. PATENT DOCUMENTS

| | | | |
|---|---|---|---|
| 5,246,867 A | 9/1993 | Lakowicz et al. | |
| 5,368,028 A | 11/1994 | Palti | |
| 5,373,855 A * | 12/1994 | Skrabal et al. | 600/563 |
| 5,381,075 A | 1/1995 | Jordan | |
| 5,387,522 A * | 2/1995 | Vasington et al. | 435/283.1 |
| 5,427,935 A | 6/1995 | Wang et al. | |
| 5,443,508 A | 8/1995 | Giampapa | |
| 5,529,066 A | 6/1996 | Palti | |
| 5,614,378 A | 3/1997 | Yang et al. | |
| 5,626,134 A | 5/1997 | Zuckerman | |
| 5,660,940 A | 8/1997 | Larsson et al. | |
| 5,702,444 A | 12/1997 | Struthers et al. | |
| 5,741,334 A | 4/1998 | Mullon et al. | |
| 5,770,454 A | 6/1998 | Essenpreis et al. | |
| 5,833,603 A | 11/1998 | Kovacs et al. | |
| 5,834,005 A | 11/1998 | Usala | |
| 5,855,613 A | 1/1999 | Antanavich et al. | |
| 5,879,709 A | 3/1999 | Soon-Shiong et al. | |
| 5,902,745 A | 5/1999 | Butler et al. | |
| 5,912,005 A | 6/1999 | Lanza et al. | |
| 5,998,204 A | 12/1999 | Tsien et al. | |
| 6,049,727 A | 4/2000 | Crothall | |
| 6,049,728 A | 4/2000 | Chou | |
| 6,061,582 A | 5/2000 | Small et al. | |
| 6,091,974 A | 7/2000 | Palti | |
| 6,163,714 A | 12/2000 | Stanley et al. | |
| 6,188,477 B1 | 2/2001 | Pu et al. | |
| 6,197,534 B1 | 3/2001 | Lakowicz et al. | |
| 6,254,601 B1 | 7/2001 | Burbank et al. | |
| 6,294,281 B1 | 9/2001 | Heller | |
| 6,368,592 B1 | 4/2002 | Colton et al. | |
| 6,400,974 B1 | 6/2002 | Lesho | |
| 6,485,703 B1 | 11/2002 | Cote et al. | |
| 6,521,446 B2 | 2/2003 | Hellinga | |
| 6,531,239 B2 | 3/2003 | Heller | |
| 6,577,393 B1 | 6/2003 | Potzschke et al. | |
| 6,584,335 B1 * | 6/2003 | Haar et al. | 600/322 |
| 6,587,704 B1 | 7/2003 | Fine et al. | |
| 6,602,251 B2 | 8/2003 | Burbank et al. | |
| 6,605,039 B2 | 8/2003 | Houben et al. | |
| 6,625,479 B1 | 9/2003 | Weber et al. | |
| 6,630,154 B1 | 10/2003 | Fraker et al. | |
| 6,650,919 B2 | 11/2003 | Edelberg et al. | |
| 6,673,596 B1 | 1/2004 | Sayler | |
| RE38,525 E | 6/2004 | Stanley et al. | |
| 6,764,488 B1 | 7/2004 | Burbank et al. | |
| 6,766,183 B2 | 7/2004 | Walsh et al. | |
| 6,846,288 B2 | 1/2005 | Nagar et al. | |
| 6,979,290 B2 | 12/2005 | Mourlas et al. | |
| 7,068,867 B2 | 6/2006 | Adoram et al. | |
| 7,184,810 B2 | 2/2007 | Caduff et al. | |
| 7,223,279 B2 | 5/2007 | Burbank et al. | |
| 7,259,906 B1 | 8/2007 | Islam | |
| 7,489,402 B2 | 2/2009 | Selker et al. | |
| 7,892,222 B2 | 2/2011 | Vardi et al. | |
| 7,951,357 B2 | 5/2011 | Gross et al. | |
| 8,088,595 B2 | 1/2012 | Ibey et al. | |
| 2002/0016535 A1 | 2/2002 | Martin et al. | |
| 2002/0025469 A1 | 2/2002 | Heller | |
| 2002/0038083 A1 | 3/2002 | Houben et al. | |
| 2002/0072657 A1 | 6/2002 | Bousquet et al. | |
| 2002/0120186 A1 | 8/2002 | Keimel | |
| 2003/0087427 A1 | 5/2003 | Colton et al. | |
| 2003/0117629 A1 | 6/2003 | Messerschmidt et al. | |
| 2003/0134346 A1 | 7/2003 | Amiss et al. | |
| 2003/0216759 A1 | 11/2003 | Burbank et al. | |
| 2003/0227681 A1 | 12/2003 | Currie | |
| 2003/0232370 A1 | 12/2003 | Trifiro | |
| 2004/0091757 A1 | 5/2004 | Wang et al. | |
| 2004/0097788 A1 | 5/2004 | Mourlas et al. | |
| 2004/0109302 A1 | 6/2004 | Yoneda et al. | |
| 2004/0111018 A1 * | 6/2004 | Isenberg et al. | 600/364 |
| 2004/0133188 A1 | 7/2004 | Vardi et al. | |
| 2004/0199059 A1 | 10/2004 | Brauker | |
| 2004/0259270 A1 | 12/2004 | Wolf | |
| 2005/0113852 A1 | 5/2005 | Burbank et al. | |
| 2005/0118726 A1 | 6/2005 | Schultz et al. | |
| 2005/0211572 A1 | 9/2005 | Buck | |
| 2005/0221072 A1 | 10/2005 | Dubrow et al. | |
| 2005/0221276 A1 | 10/2005 | Rozakis et al. | |
| 2005/0267326 A1 * | 12/2005 | Loeb et al. | 600/102 |
| 2006/0000479 A9 | 1/2006 | Burbank et al. | |
| 2006/0241365 A1 | 10/2006 | Botvinick | |
| 2007/0003994 A1 | 1/2007 | Simpson | |
| 2007/0004974 A1 | 1/2007 | Nagar et al. | |
| 2007/0066877 A1 | 3/2007 | Arnold et al. | |
| 2008/0086042 A1 | 4/2008 | Brister | |
| 2009/0178459 A1 | 7/2009 | Li | |
| 2009/0287060 A1 * | 11/2009 | Pell et al. | 600/201 |
| 2010/0037329 A1 | 2/2010 | Frommer | |
| 2010/0145317 A1 | 6/2010 | Laster et al. | |
| 2010/0160749 A1 | 6/2010 | Gross et al. | |
| 2010/0202966 A1 | 8/2010 | Gross et al. | |
| 2011/0251471 A1 | 10/2011 | Gross et al. | |
| 2012/0059232 A1 | 3/2012 | Gross et al. | |
| 2012/0113997 A1 | 5/2012 | Islam | |

FOREIGN PATENT DOCUMENTS

| | | |
|---|---|---|
| WO | 91/09312 | 6/1991 |
| WO | WO/94/00602 | 6/1994 |
| WO | 96/00106 | 1/1996 |
| WO | 98/54294 | 12/1998 |
| WO | 98/54294 A1 | 12/1998 |
| WO | 98/55869 | 12/1998 |
| WO | 01/50983 | 7/2001 |
| WO | 03/011445 | 2/2003 |
| WO | 03/025220 | 3/2003 |
| WO | 2004/028358 | 4/2004 |
| WO | 2004/051774 | 6/2004 |
| WO | 2004/089465 | 10/2004 |
| WO | 2005/033659 A2 | 4/2005 |
| WO | 2005/053523 | 6/2005 |
| WO | 2006/006166 | 1/2006 |
| WO | 2006/097933 | 9/2006 |
| WO | 2007/110867 | 10/2007 |
| WO | 2008/018079 | 2/2008 |
| WO | 2010/073249 | 7/2010 |

OTHER PUBLICATIONS

A European Search Report and communication dated Oct. 31, 2012, which issued during the prosecution of EP Patent Application No. 12 15 9273.

Communication dated Feb. 26, 2013, which issued during the prosecution of EP Patent Application No. 07736139.2.

An International Search Report and a Written Opinion both dated Nov. 21, 2012, which issued during the prosecution of Applicant's PCT/IL2012/000268.

An Extended European Search Report dated Apr. 15, 2013, which issued during the prosecution of EP Patent Application No. 09834227.2.

An English Translation of an Office Action dated Apr. 1, 2013 which issued during the prosecution of Chinese Patent Application No. 200980157599.

An Office Action dated Oct. 3, 2012, which issued during the prosecution of U.S. Appl. No. 12/344,103.

An Office Action dated Feb. 2, 2012, which issued during the prosecution of U.S. Appl. No. 12/225,749.

An Office Action dated Jan. 13, 2012, which issued during the prosecution of European Patent Application No. 0578905.3.

An International Preliminary Report on Patentability dated Jun. 29, 2011 which issued during the prosecution of Applicant's PCT/IL 09/01214.

An International Search Report and a Written Opinion both dated Jul. 1, 2010 which issued during the prosecution of Applicant's PCT/IL 09/01214.

An International Preliminary Report on Patentability dated Mar. 24, 2009 which issued during the prosecution of Applicant's PCT/IL2005/000743.

(56) References Cited

OTHER PUBLICATIONS

Written Opinion dated Mar. 20, 2009 which issued during the prosecution of Applicant's PCT/IL2005/000743.
An International Search Report dated May 7, 2009 which issued during the prosecution of Applicant's PCT/IL2005/000743.
A Supplementary European Search Report dated Dec. 16, 2009, which issued during the prosecution of Applicant's European Patent Applicant No. EP 05 75 8905.
A Supplementary European Search Report dated Mar. 3, 2010 which issued during the prosecution of Applicant's European Patent Application No. 05758905.3.
An International Search Report dated Jan. 24, 2008 which issued during the prosecution of Applicant's PCT/IL2007/000399.
An International Preliminary Report on Patentability together with Written Opinion dated Sep. 30, 2008 which issued during the prosecution of Applicant's PCT/IL2007/000399.
An Office Action dated Sep. 23, 2011 which issued during the prosecution of U.S. Appl. No. 12/225,749.
A Supplementary European Search Report dated Feb. 4, 2010 which issued during the prosecution of Applicant's European Patent Application No. 07736139.2.
An Office Action dated Nov. 16, 2011 which issued during the prosecution of European Patent Application No. 07736139.2.
U.S. Appl. No. 60/820,130, filed Jul. 24, 2006.
U.S. Appl. No. 60/658,716, filed Mar. 3, 2005.
U.S. Appl. No. 60/588,211, filed Jul. 14, 2004.
Wan Q, "Dual wavelength polarimetry for monitoring glucose in the presence of varying birefringence," A thesis submitted to the Office of Graduate Studies of Texas A&M University (2004).
Klueh U. et al., "Enhancement of implantable glucose sensor function in vivo using gene transfer-induced neovascularization," Biomaterials, Apr. 2005, 26(10):1155-63.
Yu-Lung L et al., "A polarimetric glucose sensor using a liquid-crystal polarization modulator driven by a sinusoidal signal," Optics Communications 259(1), pp. 40-48 (2006).
Olesberg JT et al., "Tunable Laser Diode System for Noninvasive Blood Glucose Measurements," Appl. Spectrosc. 59, pp. 1480-1484 (2005).
Olesberg JT et al., "In vivo near-infrared spectroscopy of rat skin tissue with varying blood glucose levels," Analytical Chemistry 78, pp. 215-223 (2006).
Ye K et al., "Genetic engineering of an allosterically based glucose indicator protein for continuous glucose monitoring by fluorescence resonance energy transfer," Analytical Chemistry, 2003, 75(14), 3451-3459.
Fillat C et al., "Suicide gene therapy mediated by the herpes simplex virus thymidine kinase gene / ganciclovir system: Fifteen years of application," Current Gene Therapy, 3(1), pp. 13-26, (Feb. 2003).
Scognamiglio V et al., "Protein-based biosensors for diabetic patients," Journal of Fluorescence, 14(5), 491-498 (Sep. 2004).
Moschou E et al., "Fluorescence glucose detection: Advances toward the ideal in vivo biosensor," Journal of Fluorescence, 14(5), 535-547 (Sep. 2004).
Reszka R et al., "Liposome-mediated suicide gene therapy in humans," Methods in Enzymology, 391, 200-208 (2005).
Deuschle K et al., "Construction and optimization of a family of genetically encoded metabolite sensors by semirational protein engineering," Protein Sci. 14: 2304-2314 (2005).
Yonzon CR et al., "A glucose biosensor based on surface-enhanced Raman scattering: Improved partition layer, temporal stability, reversibility, and resistance to serum protein interference," Anal. Chem., 76 (1), pp. 78-85 2004.
Liua L et al., "Glucose permeable poly (dimethyl siloxane) poly (N-isopropyl acrylamide) interpenetrating networks as ophthalmic biomaterials," Biomaterials vol. 26, Issue 3 pp. 233-244 (2005).
Yokota M et al., "A compact polarimetric glucose sensor using a high-performance fibre-optic Faraday rotator," Meas. Sci. Technol. 15 pp. 143-147 (2004).
McNichols J et al., "Development of a non-invasive polarimetric glucose sensor," IEEE-LEOS Newsletter, 12:30-31 (1998).

Olesberg JT, "Noninvasive blood glucose monitoring in the 2.0-2.5 μm wavelength range," Lasers and Electro-Optics Society. LEOS 2001. The 14th Annual Meeting of the IEEE. vol. 2, p. 529.
Dvir D et al., "Non invasive blood glucose monitoring in the critically ill patients," European Society for Clinical Nutrition and Metabolism Congress, Istanbul (2006)—an abstract.
Koo TW et al., "Measurement of glucose in human blood serum using Raman spectroscopy", IEEE-LEOS Newsletter 12(2) 18 (1998).
Amir O et al., "Accurate home and clinical use of a non-invasive continuous glucose monitor," (2006)—an abstract.
H.P. Bennetto, "Electricity generation by microorganisms", Biotech. Educ. vol. 1, No. 4, pp. 163-168, 1990.
K. Yamada, et al., "Measurement of glucose uptake and intracellular calcium concentration in single, living pancreatic β-cells", The Journal of Biological Chemistry, vol. 275, No. 29, Jul. 2000, pp. 22278-22283.
P. Turkewitsch, "The synthesis of fluorescent chemosensors responsive to cAMP and other nucleotides", Montreal Quebec, Sep. 1998.
G. Gilardi, et al., "Spectroscopic properties of an engineered maltose binding protein", Protein Engineering vol. 10 No. 5, pp. 479-486, 1997.
Homme W. Hellinga, et al., "Protein engineering and the development of generic biosensors", TIBTECH Apr. 1998, vol. 16.
S.P.J. Higson, et al., "Biosensors: a viable monitoring technology?", Med. & Biol. Eng. & Comput., 1994, 32, 601-609.
Leah Tolosa, et al., "Optical assay for glucose based on the luminescnence decay time of the long wavelength dye Cy5™", Sensors and Actuators B 45 (1997) 93-99.
Leah Tolosa, et al., "Glucose sensor for low-cost lifetime-based sensing using a genetically engineered protein", Analytical Biochemistry 267, 114-120 (1999).
J.C. Pickup, et al., "Fluorescence-based glucose sensors", Biosensors and Bioelectronics 20 (2005) 2555-2565.
M. Sakurada, et al., "Relation between glucose-stimulated insulin secretion and intracellular calcium accumulation studied with a superfusion system of a glucose-responsive pancreatic β-cell line MIN6", Endo. 1993, vol. 132, No. 6.
S. Tsujimura, et al., "Photosynthetic bioelectrochemical cell utilizing cyanobacteria and water-generating oxidase", Enzyme and Microbial Tech. 29 (2001) 225-231.
Deuschle, et al., "Genetically encoded sensors for metabolities", Cytometry A. Mar. 2005;64(1):3-9.
Serganova, et al., "Reporter gene imaging: potential impact on therapy", Nucl Med Biol. Oct. 2005;32(7):763-80.
Laxman, et al., "Noninvasive real-time imaging of apoptosis", Proc Natl Acad Sci USA Dec. 24, 2002;99(26):16551-5.
Fehr, et al., "In vivo imaging of the dynamics of glucose uptake in the cytosol of COS-7 cells by fluorescent nanosensors", J Biol Chem. May 23, 2003; 278(21):19127-33.
Fehr, et al., "Minimally invasive dynamic imaging of ions and metabolites in living cells", Curr Opin Plant Biol. Jun. 2004;7(3):345-51.
H.J. Philippe, et al., "Vaginal ligature of uterine arteries during post-partum hemorrhage", International Journal of Gynecology & Obstetrics 56 (1997) 267-270.
Leah Tolosa, et al., "Lifetime-based sensing of glucose using energy transfer with a long lifetime donor", Analytical Biochemistry 250, 102-108, 1997.
Pickup, et al., "In vivo glucose monitoring: the clinical reality and the promise", Biosens Bioelectron. Apr. 15, 2005;20(10):1897-902.
Olesberg JT et al., "Optical microsensor for continuous glucose measurements in interstitial fluid," Optical Diagnostics and Sensing VI, Proc. of SPIE vol. 6094, 609403, pp. 1605-7422 (2006).
Amir O et al., "Highly accurate non-invasive continuous glucose monitoring in clinical and home use settings," American Diabetes Association, 66th Scientific Session, Washington, D.C. (2006)—an abstract.
G. Patounakis, et al., "Active CMOS array sensor for time-resolved fluorescence detection", IEEE Journal of Solid-State Circuits, vol. 41, No. 11, Nov. 2006.
Primack H, "Non-invasive sensing of glucose and hemoglobin," Optical Imaging (2006)—an abstract.

(56) References Cited

OTHER PUBLICATIONS

Ackland-Berglund, C et al., "Efficacy of tetracycline-controlled gene expression is influenced by cell type," BioTechniques 18, 196-200 (1995).

Amir O et al., "Evaluation of a non-invasive continuous glucose monitoring device in a home use setting," European Association for the Study of Diabetes, 42nd Annual Meeting, Copenhagen-Malmoe, Denmark-Sweden (2006)—an abstract.

Cote GL "Noninvasive and minimally-invasive optical monitoring technologies," The Journal of Nutrition 131:1596S-1604S (2001).

Berrebi A et al., "A non-invasive evaluation of hematocrit with a new optical sensor," European Hematology Association, 11th Congress, Amstaerdam (2006).

Kononenko A et al., "Evaluation of a non-invasive blood glucose monitoring device for critically ill patients," 26th International Symposium on Intensive Care and Emergency Medicine, Brussels (2006).

J.S. Marvin, et al., "The rational design of allosteric interactions in a monomeric protein and its applications to the construction of biosensors", Proc. Natl. Acad. Sci. USA vol. 94, pp. 4366-4371, Apr. 1997.

Partial International Search Report, dated Mar. 24, 2014, which issued in PCT Application No. PCT/IB2013/061368.

International Search Report and Written Opinion, dated Jun. 12, 2014, which issued in PCT Application No. PCT/IB2013/061368.

An Office Action dated Aug. 26, 2013, which issued during the prosecution of U.S. Appl. No. 13/141,936.

An Office Action dated Aug. 26, 2013, which issued during the prosecution of U.S. Appl. No. 12/344,103.

Jithesh V. Veetil et al. "A Glucose Sensor Protein for Continuous Glucose Monitoring" Biosens Bioelectron. Dec. 15, 2010; 26(4): 1650-1655. doi:10.1016/j.bios.2010.08.052.

Sha Jin et al., "Construction of a Panel of Glucose Indicator Proteins for Continuous Glucose Monitoring", Biosens Bioelectron. Apr. 15, 2011; 26(8): 3427-3431. doi:10.1016/j.bios.2011.01.017.

Yun Jung Heo et al., "Towards Smart Tattoos: Implantable Biosensors for Continuous Glucose Monitoring" Adv. Healthcare Mater. 2013, 2, 43-56.

Steve Barash et al., "Human secretory signal peptide description by hidden Markov model and generation of a strong artificial signal peptide for secreted protein expression", Biochemicaland BiophysicalResearch Communications 294 (May 15, 2002) 835-842.

John C. Pickup et al., "Fluorescence-based glucose sensors", Biosensors and Bioelectronics 20 (2005) 2555-2565.

* cited by examiner

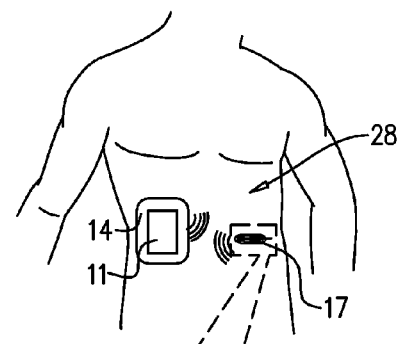
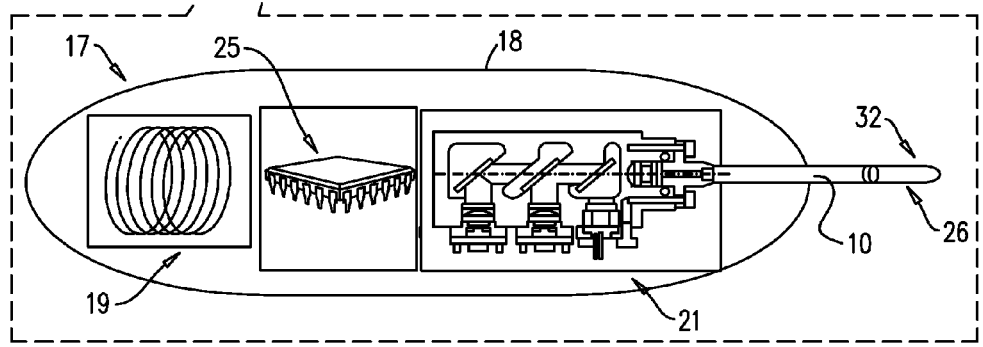
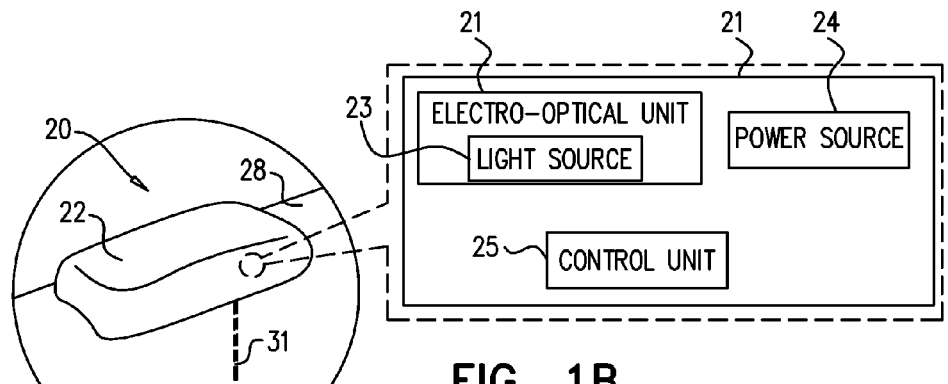
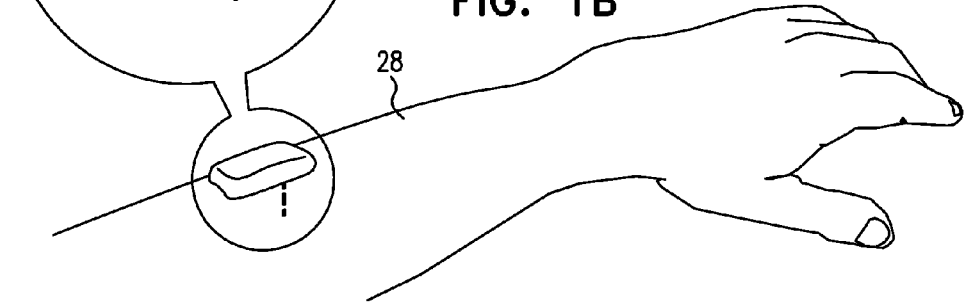
FIG. 1A
FIG. 1B

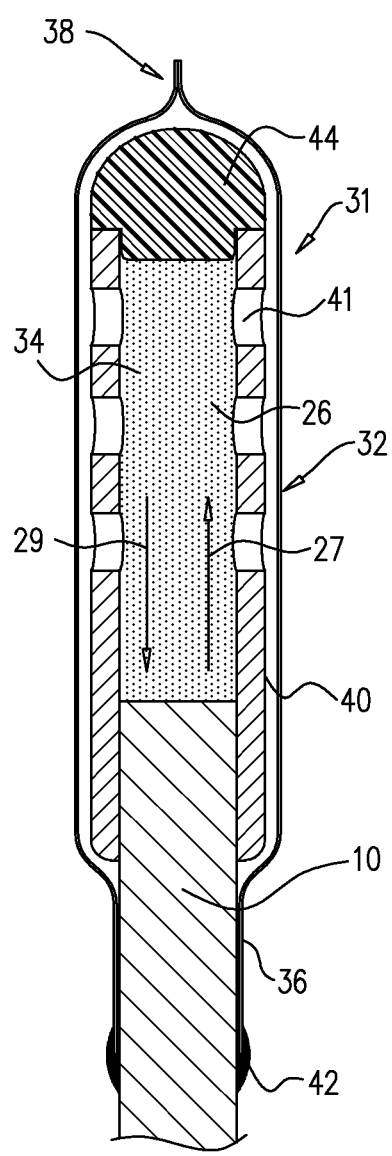
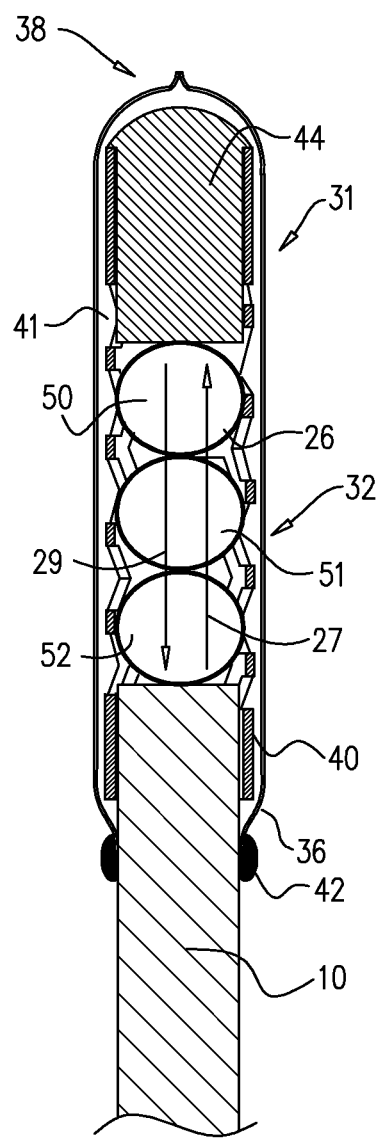

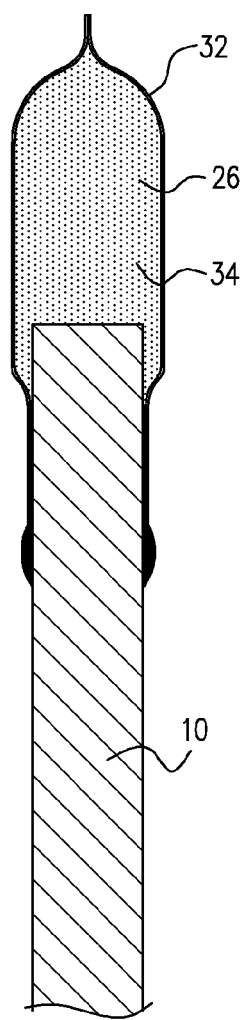
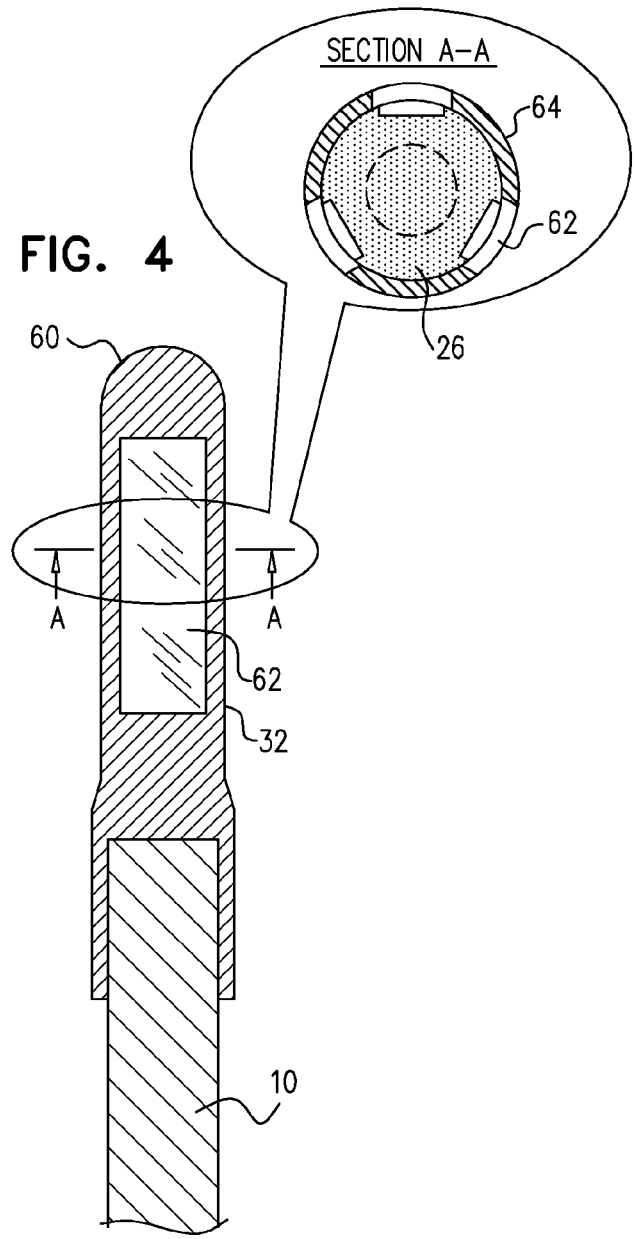

IMPLANTABLE OPTICAL GLUCOSE SENSING

FIELD OF THE INVENTION

Some applications of the present invention relate generally to implantable sensors for detecting an analyte in a body and specifically to methods and apparatus for sensing blood glucose concentrations.

BACKGROUND

Diabetes mellitus is a disease in which cells fail to uptake glucose either due to a lack of insulin (Type I) or an insensitivity to insulin (Type II). The associated elevation of blood glucose levels for prolonged periods of time has been linked to a number of problems including retinopathy, nephropathy, neuropathy, and heart disease. A typical care regimen for Type I diabetics includes daily monitoring of blood glucose levels and injection of an appropriate dose of insulin. Conventional glucose monitoring involves the use of an invasive "finger-stick" method in which the finger of a subject is pricked in order to withdraw a small amount of blood for testing in a diabetes monitoring kit based on the electroenzymatic oxidation of glucose.

Fluorescence is a photochemical phenomenon in which a photon of specific light wavelength (excitation wavelength) strikes an indicator (fluorophore) molecule, thereby exciting an electron to a higher energy state. As that "excited" electron decays back down to its original ground state, another photon of light is released at a longer wavelength (emission wavelength).

Fluorescence resonance energy transfer (FRET) involves the transfer of non-photonic energy from an excited fluorophore (the donor) to another fluorophore (the acceptor) when the donor and acceptor molecules are in close proximity to each other. FRET enables the determination of the relative proximity of the molecules for investigating, for example, molecular interactions between two protein partners, structural changes within one molecule, ion concentrations, and the binding of analytes.

SUMMARY OF THE INVENTION

In some applications of the present invention, a full-implantable or partially-implantable device is configured to have both (a) a sampling region, e.g., a chamber, configured to passively allow passage therethrough of fluid, typically interstitial fluid, from a subject, and (b) an optical measuring device which measures a parameter of an analyte, typically glucose, in the sampling region. Typically, the sampling region is subcutaneously implanted within the subject. Typically, the optical measuring device is subcutaneously implanted as well, e.g., in a common housing with the sampling region. For some applications, the optical measuring device is configured to be placed on the skin and to measure a concentration of the analyte, e.g., glucose, in biological fluid of the subject. The optical measuring device typically comprises a light source, i.e., a system providing visible or non-visible light, a control unit, a power source and a detection system.

In some applications, a mechanism for attaching the device to the body is utilized as well as an insertion mechanism for implanting the implantable sampling region. Typically, the attaching device comprises a sensor support device (not shown), which is attached to the subject by an adhesive pad. In some applications, the sensor support device comprises a channel for orienting a hypodermic insertion needle configured to insert a sampling region under the skin of the subject. In further applications, the sensor support device is configured to place an external connector (not shown) in position for connection to the optical measuring device. Subsequently, in preparation for regular use of the apparatus, the hypodermic needle is removed from the skin.

In some applications the optical measuring device and sampling region are both implanted subcutaneously. An insertion trocar, or in some instances, a hypodermic insertion needle, is used to place the device at one of a range of depths, as appropriate for the implantation site.

The light from the light source is typically conveyed to the sampling region via an optical fiber attached to the sampling region. In some applications, more than one light source is used. Typically, the same fiber allows signals to be returned to the optical measuring device from the sampling region. In some applications, fibers are split and the signals are split among more than one measuring device. Typically, the sampling region is implanted in the body of the subject, and comprises a semi-permeable membrane which is permeable to the analyte. The membrane is attached to the distal end of the optical fiber and encases the sampling region by being fitted over the distal end of the fiber. In some applications of the present invention, the sampling region contains an optically-transparent and glucose-permeable material, e.g., a gel or polymer, configured to define the sampling region.

Alternatively or additionally, the sampling region is surrounded by a selectively-permeable membrane which restricts passage therethrough of substances, e.g., cells, which could potentially interfere with the measuring of the parameter of the fluid. The membrane may surround the sampling region independently of, or in combination with, the transparent glucose-permeable material contained within the sampling region. Typically, the membrane is configured to restrict passage, into the sampling region, of cells and some molecules having a molecular weight greater than the molecular weight of the analyte configured to be measured by the device. In some applications of the present invention, the sampling region comprises genetically-engineered cells that produce a protein that is able to bind with the analyte and to undergo a conformational change in a detectable manner. Alternatively, the protein is placed in the sampling region without cells. The optical measuring device detects the conformational change, via a signal generated indicative of a level of the analyte in the subject. The signal itself is embodied as the amount of light of different wavelengths emitted by the protein. Typically, but not necessarily, FRET techniques—i.e., Förster resonance energy transfer, also known as fluorescence resonance energy transfer, are used to detect the conformational change. These genetically-engineered cells may be used in combination with the detection methods described hereinbelow.

Combined, the membrane and the material in the sampling region are designed such that the glucose in the sampling region is generally in equilibrium with the interstitial level of glucose or alternatively, with the level of glucose in other bodily fluids into which the sampling region is implanted.

Biological material in the sampling region, typically genetically-engineered proteins or cells containing genetically-engineered protein, convey, typically via FRET, a signal to the optical measuring device, typically via an optical fiber, for determination of glucose level. In some applications, an external device can, based on the glucose level, automatically provide insulin to the subject, if medically indicated.

Alternatively, the device is configured to be a fully implantable device that communicates wirelessly through the skin of the subject. In some applications, power transmission, data transmission and/or excitation light (typically 488 nm or another suitable wavelength), are also provided through the skin of the subject (the power and data being transmitted wirelessly, or in a wired configuration). Light emitted from within the device may pass to a detector outside of the subject's skin, either through tissue or via one or more optical fibers. In further applications, genetically-engineered proteins, employed in the sample region, emit red or infrared fluorescent light in response to the presence of the analyte, e.g., using techniques described in an article by Steinmeyer R et al., entitled, *Improved fluorescent proteins for single-molecule research in molecular tracking and co-localization*, J Fluoresc. 2005 September; 15(5):707-21. This emitted light may be sensed by devices external to the skin, as is known in the art.

There is therefore provided, in accordance with an application of the present invention, apparatus for detecting an analyte, configured to be implanted in a body of a subject, the apparatus including: an optical fiber having a distal portion; and a membrane permeable to the analyte, the membrane coupled to the distal portion of the fiber and surrounding a sampling region at least in part, by being fitted over the distal portion of the fiber.

In some applications, the optical fiber includes exactly one optical fiber.

In some applications, the membrane is attached to the distal portion of the fiber within 5 mm of a distal tip of the fiber.

In some applications, the membrane is attached to the distal portion of the optical fiber by glue.

In some applications, the apparatus includes a perforated tube surrounding the sampling region.

In some applications, the membrane surrounds the perforated tube.

In some applications, the perforated tube surrounds the membrane.

In some applications, the distal portion of the optical fiber is disposed within the perforated tube.

In some applications, the perforated tube includes a material selected from the group consisting of: metal and plastic.

In some applications, the sampling region has a shape selected from the group consisting of cylindrical and hemispherical.

In some applications, the membrane is shaped to define a hole therein that is sealed, the sealed hole located at a distal end of the sampling region relative to the optical fiber.

In some applications, the apparatus includes a stopper inserted into a distal end of the perforated tube relative to the optical fiber.

In some applications, the apparatus includes a light source configured to pass light through the optical fiber toward the sampling region; and a detection system, configured to receive fluorescent light, through the optical fiber, from the sampling region, and to analyze the fluorescent light in order to determine an indication of a level of the analyte in the body of the subject.

In some applications, the detection system is configured to facilitate administration of a substance to the subject, in response to the determined indication of the level of the analyte.

In some applications, the detection system is configured to determine the indication of the level of the analyte, while outside of the body of the subject.

In some applications, the detection system is configured to be implanted in the body of the subject, and to determine the indication of the level of the analyte, while inside the body of the subject.

In some applications, the sampling region includes biological matter, which changes a state thereof in response to a concentration of the analyte in the subject.

In some applications, the biological matter includes a plurality of fluorescent proteins including a genetically-modified glucose receptor protein, and a cyan fluorescent protein (CFP) and a yellow fluorescent protein (YFP) coupled to the glucose receptor protein, and is configured such that when a glucose molecule from the subject interacts with the genetically-modified glucose receptor protein, the glucose receptor protein changes conformation as a result, and the two fluorescent proteins are in close enough proximity to each other so that the CFP acts as an energy donor and the YFP acts as an energy acceptor in a Fluorescence Resonance Energy Transfer (FRET) signaling system that indicates a concentration of glucose through the emission of electromagnetic radiation.

In some applications, the biological matter includes a plurality of cells, which produce the genetically-modified glucose receptor proteins.

In some applications, the apparatus includes one or more alginate beads encasing the biological matter.

In some applications, each bead has a diameter of 40 um to 150 um.

In some applications, each bead has a diameter of 150 um to 600 um.

In some applications, the apparatus includes a perforated tube surrounding the sampling region, wherein each bead has a diameter equal to 60% to 80% of the internal diameter of the perforated tube.

In some applications, each bead has a diameter equal to 80% to 120% of a diameter of the optical fiber.

In some applications, the one or more alginate beads include exactly two alginate beads.

In some applications, the one or more alginate beads include exactly three alginate beads.

There is further provided, in accordance with an application of the present invention, apparatus for detecting an analyte, configured to be implanted in a body of a subject, the apparatus including an optical fiber having a distal portion; a first perforated tube having a distal and a proximal end, the first perforated tube surrounding at least in part a sampling region by being fitted over the distal portion of the optical fiber; a membrane permeable to the analyte and surrounding the first perforated tube; and a second perforated tube having a distal end, surrounding the membrane.

In some applications, at least one of the tubes is closed at the distal end thereof.

In some applications, the second perforated tube is attached to the membrane by glue.

In some applications, the first perforated tube is attached to the optical fiber by glue.

In some applications, the membrane is attached to each of the perforated tubes by glue.

In some applications, at least one of the perforated tubes includes a material selected from the group consisting of metal and plastic.

There is further provided, in accordance with an application of the present invention, an apparatus for detecting an analyte, configured to be implanted in a body of a subject, the apparatus including: a first tube having a distal end and a proximal end; a membrane permeable to the analyte, coupled to the distal end of the first tube; a second tube fitted on the first tube; and an optical fiber having a distal end fitted within the proximal end of the first tube.

In some applications, the apparatus includes a ring coupled to the optical fiber, and configured to limit insertion of the optical fiber within the first tube.

In some applications, the second tube is coupled to the first tube by a sealing material configured to inhibit fluid from outside the apparatus from entering a space between the first and second tubes.

In some applications, the first and second tubes are positioned to provide a space adjacent to the membrane, and wherein the apparatus further includes an optically-transparent, glucose-permeable material disposed within the space.

In some applications, the apparatus includes a sensor proteins disposed in the material.

In some applications, the apparatus includes cells that generate the sensor proteins, disposed in the material.

In some applications, the apparatus includes one or more alginate beads, wherein the sensor proteins are disposed within the alginate beads.

In some applications, the one or more beads are squeezed between the membrane and the optical fiber.

There is further provided, in accordance with an application of the present invention, apparatus for detecting a concentration of an analyte, the apparatus being configured to be implanted in a body of a subject and configured for use with an extracorporeal detecting system, the apparatus including: a ring surrounding a sampling region, the sampling region including a fluorescent material; and one or more optical fibers coupled to the ring and configured to convey light between the sampling region and the extracorporeal detecting system.

In some applications, the one or more optical fibers include are divided into at least two bundles, a first one of the bundles configured to carry light to the sampling region, and a second one of the bundles configured to carry light away from the sampling region.

In some applications, the one or more optical fibers include a plurality of optical fibers, each of the optical fibers being coupled to a respective site on the ring.

In some applications, the apparatus includes the extracorporeal detecting system, and wherein the extracorporeal detecting system is configured to perform a FRET analysis of molecules in the sampling region.

In some applications, the one or more optical fibers include a plurality of optical fibers, wherein the ring is shaped to define a plurality of holes therein, and wherein a respective one of the optical fibers is at least partially disposed within each one of the holes.

In some applications, each one of the holes is oriented in a radial direction with respect to a center of the ring.

In some applications, the holes are evenly distributed around the ring.

There is further provided, in accordance with an application of the present invention, apparatus for detecting a concentration of an analyte, the apparatus configured to be in communication with a sampling region, the apparatus including: an antenna; an electro-optical unit, in communication with the antenna, the electro-optical unit including: one or more filters and one or more mirrors; at least one light source configured to convey one or more wavelengths of light to the sampling region, the light source being in communication with the one or more filters and one or more mirrors; one or more beam splitters; and a detector configured to receive one or more wavelengths of light from the sampling region, the detector being in communication with the one or more beam splitters and one or more mirrors.

In some applications, the electro-optical unit is configured as a free-space optics system.

In some applications, the apparatus includes at least one optical fiber, wherein the electro-optical unit is configured to use the at least one optical fiber to convey light from the light source to the sampling region, and further, to use the at least one optical fiber to convey light from the sampling region to the detector.

In some applications, the apparatus is configured to be implanted within a subject.

In some applications, the apparatus is configured to be: coupled extracorporeally to a subject and in communication with the sampling region when the sampling region is within the subject.

In some applications, the antenna is configured to transmit data.

In some applications, the antenna is configured to receive power.

In some applications, the apparatus includes a reservoir configured to hold a substance; and at least one pump, configured to pump a measured amount of the substance from the reservoir into a subject, in response to a signal from the electro-optical unit.

In some applications, the pump is configured to avoid influencing measurements of the electro-optical unit.

In some applications, the apparatus includes a tube configured to convey the substance from the reservoir to the subject, a distal end of the tube configured to be at least 0.5 mm from the sampling region when the pump pumps the substance.

In some applications, that distance is less than 5.0 mm.

In some applications, the reservoir is configured to hold insulin.

There is further provided, in accordance with an application of the present invention, apparatus for detecting a concentration of an analyte in a sampling region, the apparatus configured to be implanted in a body of a subject, the apparatus including: an electro-optical unit including a light source; a first set of one or more optical fibers configured to transmit light in exactly one direction, from the light source toward the sampling region; and a second set of one or more optical fibers configured to transmit light in exactly one direction, from the sampling region toward the electro-optical unit.

There is further provided, in accordance with an application of the present invention, apparatus for detecting an analyte, configured to be implanted in a body of a subject, the apparatus for use with an electro-optical unit and including: at least one bead; and an optical fiber having a distal portion within 10 mm of the bead and in optical communication with an interior of the bead, the bead being in a compressed state while in optical communication with the optical fiber.

In some applications, the at least one bead includes two beads.

In some applications, the at least one bead includes three beads.

In some applications, the bead is spherical, if placed in an uncompressed state.

In some applications, the bead is compressed by the optical fiber, from a spherical state of the bead, by 5-50% of an uncompressed diameter of the bead.

In some applications, the bead is compressed by the optical fiber, from the spherical state, by 10-30% of the uncompressed diameter of the bead.

There is further provided, in accordance with an application of the present invention, apparatus for detecting an analyte, the apparatus configured to be fully implanted in a body of a subject, the apparatus including: a capsule, including: an electro-optical unit; a control unit; and a transceiver, configured to be driven by the control unit to transmit a signal indicative of a level of the analyte detected by the electro-optical unit; and an optical fiber coupled to the electro-optical unit, the optical fiber including a distal portion outside the capsule; and a membrane permeable to the analyte, the membrane coupled to the distal portion of the optical fiber and surrounding a sampling region at least in part, by being fitted over the distal portion of the fiber.

There is further provided, in accordance with an application of the present invention, apparatus for detecting an analyte, configured to be fully implanted in a body of a subject, the apparatus including: a capsule, including: an electro-optical unit; a control unit; a transceiver, configured to be driven by the control unit to transmit a signal indicative of a level of the analyte detected by the electro-optical unit; and a lens coupled to the electro-optical unit; and a membrane permeable to the analyte, the membrane coupled to an external surface of the capsule and surrounding a sampling region, and configured to receive light from the electro-optical unit via the lens.

The present invention will be more fully understood from the following detailed description of some applications thereof, taken together with the drawings, in which:

BRIEF DESCRIPTION OF THE DRAWINGS

FIG. 1A is a schematic illustration of a mostly-encapsulated injectable device comprising an optical measuring device, power source and control unit and sampling region, configured to be implanted subcutaneously within the body of the subject, in accordance with some applications of the present invention;

FIG. 1B is a schematic illustration of a support for an optical measuring device, power source and control unit configured to be coupled to the body of a subject, and that is further coupled to a sampling region configured to be inserted into the body of the subject, in accordance with some applications of the present invention;

FIGS. 2A-B are schematic illustrations of subcutaneously-implanted membrane-covered sensors containing a sampling region for detecting an interstitial analyte, in accordance with some applications of the present invention;

FIGS. 3-8 are further schematic illustrations of subcutaneously-implanted membrane-covered sensors, in accordance with some applications of the present invention;

DETAILED DESCRIPTION OF THE EMBODIMENTS

Figure 8:
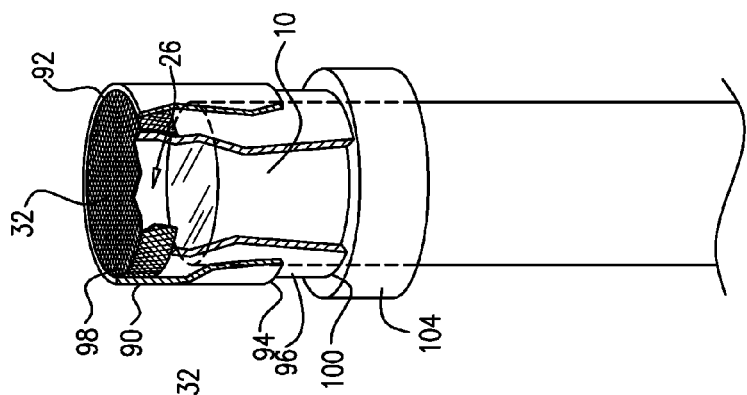

Reference is now made to FIG. 1A, which is a schematic illustration of an injectable device 17 comprising an electro-optical unit 21, a power source (not shown), a control unit 25, and a transceiver 19, in accordance with some applications of the present invention. The device is typically fully encapsulated in a capsule 18.

In some applications, capsule 18 is made of glass. In some applications, the capsule is made from other materials known in the art that are suitable to be implanted in the human body.

An optical fiber 10 is coupled to electro-optical unit 21 at one end of injectable device 17. A proximal portion of optical fiber 10 is within capsule 18. A distal portion extends out from capsule 18, to reach a sampling region 26 that is coupled to the distal portion of optical fiber 10.

Sampling region 26, typically bounded by a selectively-permeable membrane 32, is in some applications similar to sampling regions described hereinbelow with reference to FIGS. 2-9.

Typically, injectable device 17 has a diameter of 2-4 mm (e.g., 3 mm) and a length of 7-13 mm (e.g., 10 mm).

In some applications, injectable device 17 is injected under the surface of the skin of subject via a large bore needle or cannula (not shown). In other applications, the device is implanted via an incision in the skin of the subject. In further applications, injectable device 17 is implanted in the subject by other methods known in the art.

Injectable device 17 is configured to be fully implantable in the subject. Injectable device 17 is, in some applications, configured to be in communication, typically via transceiver 19, with an extracorporeal power supply (not shown) and/or an extracorporeal receiver (not shown). Typically, the extracorporeal power supply is configured to wirelessly power and/or recharge injectable device 17 via methods known in the art. In some applications, injectable device 17 is configured to receive energy wirelessly, by an antenna in the subject's bed (not shown), or by an RF-emitting patch (not shown) placed on the subject's skin.

In some applications, the extracorporeal receiver is configured to send and/or receive data to and/or from injectable device 17. In further applications, the extracorporeal receiver is configured to display data relating to concentrations of an analyte (e.g., glucose) within sampling region 26. In some applications, the extracorporeal receiver is configured to transfer data received from injectable device 17 to a computer (not shown) for viewing and/or analysis.

In some applications, injectable device 17 is configured to be in communication with an extracorporeal pump 14. The extracorporeal pump is typically coupled to a reservoir and is configured to pump a substance, e.g., insulin, (for example, a measured amount of insulin), into the body of the subject in response to a signal from injectable device 17. Typically, the signal from injectable device 17 is sent in response to glucose sensing performed by electro-optical unit 21 in injectable device 17.

In some applications, the power source for extracorporeal pump 14 also provides RF energy transmission to power injectable device 17.

In further applications, extracorporeal pump 14 further comprises a replaceable cartridge 11 in lieu of or in addition to the reservoir, which further contains a power source (not shown) configured to run the pump and provide power to and/or recharge injectable device 17.

Reference is now made to FIG. 1B, which is a schematic illustration of a measuring device 20 comprising a typically extracorporeal detection system 22 which comprises an electro-optical unit 21, a power source 24 and a control unit 25, in accordance with some applications of the present invention. Typically, extracorporeal detection system 22 is held onto skin of a subject via a patch or adhesive bandage.

In some applications of the invention, there is also a transmitter (not shown) configured to send data wirelessly, e.g., from control unit 25 to a display unit, a cell phone, or an internet-connected device (not shown). Typically, measuring device 20 provides the subject with constant glucose monitoring. In some applications, measuring device 20 provides information regarding the subject's glucose levels only on demand, e.g., when measuring device 20 is in communication with a separate device (not shown).

Measuring device 20 further comprises an intracorporeal element 31. Typically, device 20 is configured to detect and measure a concentration of an analyte, e.g., glucose, in interstitial fluid of a subject. (In the context of the specification, examples of the analyte being glucose are by way of illustration and not limitation.) Typically, a sampling region 26 (see FIGS. 2A-8) of device 20 is designated for subcutaneous implantation under the skin 28 of the subject. Alternatively, the sampling region can be implanted either in blood vessels, peritoneum, the cerebrospinal fluid (CSF), or bone marrow.

In some applications, a non-FRET sensor is implanted in the subject, in conjunction with sampling region 26. In these applications, data from two or more methods (e.g., FRET and non-FRET) are combined and processed in the extracorporeal detection system 22 to provide additional or overlapping data.

In further applications, extracorporeal detection system 22 is alternatively configured to be implanted in a subject (and not to be extracorporeal). In some applications, extracorporeal detection system 22 is configured to receive power and transmit data wirelessly.

In some applications of the present invention, a light source 23 (a component of electro-optical unit 21), comprises one or more of any suitable light source, e.g., but not limited to, a light emitting diode (LED), an organic light emitting diode (OLED), a laser diode, or a solid-state laser.

Reference is now made to FIGS. 2-8, which are schematic illustrations of portions of device 20, particularly intracorporeal element 31, in accordance with various aspects of the present invention. In the absence of an indication to the contrary, all of the embodiments described hereinbelow are configured to either be fully-implantable as described hereinabove with reference to FIG. 1A or in the alternative, configured to be coupled to an extracorporeal detection system described hereinabove with reference to FIG. 1B.

In some applications of the present invention, sampling region 26 is bounded by a selectively-permeable membrane 32. In some applications of the present invention, membrane 32 is optically transparent.

In some applications, membrane 32 is optically opaque, configured to prevent spectral distortion of the detected fluorescent emission.

In some applications, the membrane is configured to provide isolation from the subject's immune system.

Typically, membrane 32 is permeable to molecules having a molecular weight equal to or less than the molecular weight of the analyte (e.g., glucose) configured to be measured by device 20, and membrane 32 is configured to restrict passage into sampling region 26 of cells from outside device 20.

Sampling region 26 typically comprises an optically-transparent and glucose-permeable material 34. In some applications, of the present invention, material 34 comprises, by way of illustration and not limitation, alginate, agarose, silicone, a polymer, a co-polymer polyethylene glycol (PEG), and/or gelatin. Alternatively or additionally, material 34 comprises a glucose-permeable gel comprising extracellular matrix (ECM), in combination with or separately from one or more of the above-listed optically-transparent and glucose-permeable materials. For some applications of the present invention, material 34 comprises an optically-transparent and glucose-permeable copolymer, e.g., Poly (dimethyl siloxane) (PDMS), Poly (N-isopropyl acrylamide) (PNIPAAM), or other optically-transparent and glucose-permeable copolymers, or other copolymers known in the art. In some applications of the present invention, material 34 comprises a plurality of hollow capillary fibers configured for optical transmission of the light from source 23 through an optical fiber 10 and to allow for passage of certain constituents (e.g., small molecules such as glucose) of fluid through sampling region 26, in order to facilitate optical measuring of the analyte in sampling region 26.

A single optical fiber 10 is shown by way of example in some of the figures. Other applications include split fibers, to allow for one or more transmissions of light back to extracorporeal detection system 22.

Typically, material 34 is configured to passively allow passage therethrough of certain constituents (e.g., small molecules such as glucose) of the interstitial fluid of the subject that have a molecular weight smaller than the desired molecular weight cutoff defined by material 34. For example, the molecular weight cutoff allows passage therethrough of glucose molecules present in the interstitial fluid. In some applications of the present invention, the molecular weight cutoff allows passage through material 34 of only glucose molecules present in the interstitial fluid and of other molecules having a molecular weight equal to or less than the molecular weight of the glucose molecule. That is, material 34 is configured to restrict passage therethrough into sampling region 26 of some molecules having a molecular weight greater than a molecular weight of a glucose molecule.

Because of the typically small size of sampling region 26, the concentration of the analyte outside of device 20 is in general equilibrium with the average concentration of analyte in the fluid measured in sampling region 26 during measurements thereof. Therefore, measuring the concentration of glucose in sampling region 26 provides an indication of the concentration of glucose in the body of the subject.

It is to be noted that membrane 32 is shown by way of illustration and not limitation. For example, material 34 of sampling region 26 may be disposed within an area defined by a support and/or upon a scaffold (e.g., as described with reference to FIG. 4) independently of or in combination with membrane 32. The scaffold may comprise a porous material configured to allow passage therethrough into region 26 of constituents of the interstitial fluid having a molecular weight smaller than the desired molecular weight cutoff defined by the scaffold. Typically, the scaffold is configured to restrict passage of cells into sampling region 26. The scaffold may be used independently of or in combination with membrane 32.

Typically, material 34 has a refractive index, which prevents or minimizes loss of light and refraction thereof.

Typically, light source 23, transmits light through sampling region 26 and away from detection system 22 in the direction indicated by arrow 27 in FIGS. 2A-B. Light returns through sampling region 26, toward detection system 22, as indicated by arrow 29.

Control unit 25, as shown in FIG. 1B, e.g., a microprocessor, is typically in communication with the other components of detection system 22, and facilitates real-time quantitative analysis of glucose in sampling region 26. Typically, the control unit drives light source 23 to emit light through fiber 10 within sampling region 26 in accordance with various emission parameters, such as duty cycle (e.g., number and/or timing of measurements per hour), wavelengths, and amplitudes.

In some applications of the present invention, control unit 25 is coupled to a drug administration unit (not shown), which is configured to administer a drug in response to the measured parameter, e.g., in response to the level of glucose measured in the interstitial fluid. In some applications of the present invention, the drug administration unit comprises an insulin pump, which supplies insulin or another drug to the body in response to the level of the analyte determined by device 20.

In some applications, the concentration of the analyte is measured using polarimetric techniques which measure the concentration of the analyte according to the polarization of light that passes from light source 23 and through sampling region 26. In such an application, polarizing filters (not shown) are disposed in optical communication with light source 23 and/or the detection system 22.

Alternatively or additionally, the concentration of the analyte is measured using absorbance spectroscopy techniques. In such an application, the absorbance spectroscopy is used to directly measure the concentration of the analyte in sampling region 26.

Alternatively or additionally, the absorbance spectroscopy device comprises a plurality of detectors (not shown) configured to detect optical scattering of the illuminated light (the scattering being induced by the presence of the analyte in the fluid). The plurality of detectors is configured to increase the signal-to-noise ratio.

Reference is now made to FIG. 2A, which is a schematic illustration of a portion of device 20 as described hereinabove with reference to FIG. 1B, in accordance with some applications of the present invention.

Typically, membrane 32 is shaped to define a substantially tubular structure for the sampling region. Sampling region 26 and membrane 32, however, are tubular structures, by way of illustration and not limitation. The tubular structure, as defined by the shaped membrane 32 is typically cylindrical or hemispherical. In other applications, other geometries known in the art can also be used. As shown, this selectively-permeable, biocompatible membrane 32 is disposed around sampling region 26, and is configured to restrict passage of some or all biomaterials into sampling region 26. In some applications of the present invention, membrane 32 comprises a hydrophobic membrane, e.g., a nitrocellulose membrane, or a polyvinylidene difluoride (PVDF) membrane, or a polytetrafluoroethylene (PTFE) membrane, or a polysulfone membrane. In some applications of the present invention, membrane 32 has a molecular weight cutoff of around 500 kDa. It is to be noted, however, that applications described herein may be implemented independently of membrane 32.

In some applications of the present invention, membrane 32 has an initially open end 36 and another initially open end 38 (i.e., a hole), and is glued with glue 42 (or another sealing element) at open end 36 to form a tight seal between membrane 32 and optical fiber 10, which is fitted into open end 36. The optical fiber typically has a diameter of 0.05 to 0.5 mm, e.g., 0.1 mm. In other applications, the seal is created using a metal or plastic ring or spring that has the properties of exerting a radial pressure on the membrane in order to seal it along the perimeter of the optical fiber. In some applications, the metal ring comprises a medical grade metal, as known in the art, treated and cut so as to maintain its shape after being pressed into position. In some applications, the plastic ring is made from a medical grade plastic, as known in the art, that is either elastic and flexible, or can be heat-shrunk, to produce the desired durable radial pressure to seal opening 36 of membrane 32. In further applications, a metal ring is configured to provide the radial pressure, and a plastic ring (e.g., comprising silicone) serves as a seal at the interface between the membrane and the optical fiber, or, the interface between the membrane and the metal ring, or, both.

Optical fiber 10 typically extends from extracorporeal detection system 22 to intracorporeal element 31. In some applications, optical fiber 10 extends from an intracorporeal detection system (not shown) to intracorporeal element 31.

Openings 36 and 38 are shown at the portions of membrane 32 that define the two longitudinal ends of membrane 32 by way of illustration and not limitation, and for some applications, one or both of the openings are not provided. For example, membrane 32 may provide only one opening. It is to be further noted that membrane 32 is shaped to define a substantially tubular structure by way of illustration and not limitation. For example, intracorporeal element 31 may comprise a flat surface that defines sampling region 26.

Typically, membrane 32 is sealed at second end 38 of sampling region 26 by glue. Alternatively a heat source may be used to create a seal by welding the membrane to itself.

For some applications of the invention, a perforated tube 40 having one or more perforations 41 in its lateral wall is placed within sampling region 26, providing for a region within the tube for sampling the analyte. Typically, perforated tube 40 is constructed from metal, but may alternatively comprise another material, as known in the art. In some applications, the perforated tube is constructed such that it has a low wall thickness, e.g., 0.01-0.05 mm, to reduce the length of the diffusion path from outside of membrane 32 to the material 34 inside the sampling region.

In some applications, perforated tube 40 has relatively large perforations through the wall of the tube, e.g., 0.02-0.06 mm in diameter, in order to increase the diffusion through the wall. Typically, perforated tube 40 is constructed such that it can maintain its rigidity and shape so that it remains generally straight (in order to minimize interference with passage of light within the tube), even if small forces are applied to the tube in situ or during insertion of all, or portions of intracorporeal element 31 into the subject.

It is noted that sampling region 26 within perforated tube 40 is described hereinabove as containing material 34 (e.g., an optically-transparent and glucose-permeable material, as described hereinabove), by way of illustration and not limitation. For example, sampling region 26 may be hollow.

Typically, optical fiber 10 fits within perforated tube 40. A stopper 44, typically of silicone, but may be other materials known in the art, is in some applications, fitted in the opposite end of tube 40, as shown.

For some applications, sampling region 26 contains cells (not shown) that are genetically engineered to express a protein configured to facilitate optical quantification of the analyte in sampling region 26. The cells are engineered to produce a molecule (e.g., a protein, or "fluorescent material," as described hereinabove) that binds with an analyte and undergoes a conformational change in a detectable manner. Typically, but not necessarily, FRET techniques known in the art are used to detect the conformational change.

For some applications of the present invention in which FRET is used, cells are genetically engineered to produce, in situ, sensor proteins (not shown) comprising a fluorescent protein donor (e.g., cyan fluorescent protein (CFP)), a fluorescent protein acceptor (e.g., yellow fluorescent protein (YFP)), and a binding protein (e.g., glucose-galactose binding protein) for the analyte. As appropriate, the sensor proteins may generally reside in the cytoplasm of cells and/or may be targeted to reside on the cell membranes of cells, and/or may be secreted by cells into sampling region 26. For some applications, the sensor proteins may be in sampling region 26, exclusive of cells. The sensor proteins are configured such that binding of the analyte to the binding protein changes the conformation of the sensor proteins, and thus the distance between respective donors and acceptors. It is to be noted that although CFP and YFP proteins are coupled to the analyte-binding protein, any fluorescent protein may be coupled to the analyte-binding protein.

In some applications, sampling region 26 has a diameter of between 0.05 and 0.5 mm and height between 0.1 and 2 mm.

FIG. 2B is a schematic illustration of sampling region 26 in perforated tube 40, as described hereinabove with reference to FIG. 2A, with the exception that sampling region 26 contains three beads 50, 51 and 52. In some applications, the perforations are limited in size to prevent the beads from escaping the tube, and the tube in general has an inner diameter suitable to maintain the beads in a generally-fixed position.

Three beads are shown for illustrative purposes, other combinations of one or more beads are also used. Beads 50 and/or 51 and/or 52 are typically spherical in shape and designed to fit within the diameter of sampling region 26.

Typically, the beads each have a diameter of 40 to 500 μm. In some applications, each bead has a diameter equal to 60% to 80% of a diameter of the perforated tube. Alternatively or additionally, each bead has a diameter equal to 80% to 120% of a diameter of the optical fiber 10.

In some applications, optical fiber 10 is configured to compress the one or more beads. Beads 50 and/or 51 and/or 52, initially spherical, are typically compressed to increase the ratio of their geometric surface area relative to volume. In addition, compressing the bead improves optical coupling between the beads and optical fiber 10. In some applications, the diameter of the beads is 50-500 microns (e.g., 100-250 microns) before being compressed. In some applications, the compression is 5-50%, for example 10-30%.

The size of perforations 41 as drawn in the figure are for illustrative purposes only and are not necessarily to scale. Perforations 41 in perforated tube 40 are, in some applications, slightly smaller than the diameter of the beads, keeping the beads in place and preventing their escape from the tube, while retaining a relatively large opening for the purpose of facilitating liquid penetration and diffusion of the measured analyte into sampling region 26 and into beads 50 and/or 51 and/or 52.

In some instances, perforations 41 in perforated tube 40 reach the end of optical fiber 10 (as illustrated). Alternatively, the perforations only exist at a distal portion of tube 40, but are not at a portion of the tube in the vicinity of the optical fiber. Typically, perforations 41 are generally evenly distributed along perforated tube 41.

By way of illustration and not limitation, three beads, i.e., beads 50 and/or 51 and/or 52, are shown in FIG. 2B as being disposed in perforated tube 40, although other bead combinations may also be used. Typically, beads 50 and/or 51 and/or 52 comprise alginate, although other materials that are permeable to interstitial glucose may also be used. Typically, beads 50 and/or 51 and/or 52 further contain genetically-modified glucose binding proteins as described hereinabove with reference to FIG. 2A. Alternatively or additionally, beads 50 and/or 51 and/or 52 further contain genetically-modified cells that produce the genetically-modified glucose binding proteins, as described hereinabove with reference to FIG. 2A.

In some applications, sampling region 26 is configured to provide a short distance for light to travel from optical fiber 10 to beads 50 and/or 51 and/or 52. In some applications, sample region 26 is configured to provide good optical coupling between bead 50 and optical fiber 10. Typically, beads 50 and/or 51 and/or 52 are pressed toward optical fiber 10 by stopper 44. In some instances, bead 52 is in direct contact with optical fiber 10.

In some applications, stopper 44 is configured to prevent slip of beads 50 and/or 51 and/or 52, and to maintain tight packing of the inside of sampling region 26, to increase the optical access of light source 23 to the beads.

FIG. 3 is a schematic illustration of sampling region 26, as described hereinabove with reference to FIGS. 2A-B, with the exception that sampling region 26 is surrounded by a membrane 32, and is not surrounded by a perforated tube, in accordance with some applications of the present invention. In some applications of the present invention, membrane 32 is shaped to define a tube, by way of illustration and not limitation. For example, membrane 32 may be shaped to define a rectangular housing, a hemisphere, or another shape. Sampling region 26, as shown, within membrane 32, comprises optically-transparent and glucose-permeable material 34 (as described hereinabove with reference to FIGS. 1, 2A and 2B), by way of illustration and not limitation.

In some applications, sampling region 26 has a diameter of between 0.05 and 0.5 mm and height between 0.1 and 2 mm.

FIG. 4 is a schematic illustration of sampling region 26, as described hereinabove with reference to FIGS. 2A-B, with the exception that sampling region 26 is contained within a perforated tube 60. Perforated tube 60 is formed such that areas of the tube have been cut out to create a scaffolding structure with windows 62. Typically, windows 62 are sized to maintain rigidity of perforated tube 60, e.g., the tube retains its general shape during and after implantation in the subject. In some instances, the windows are sized such that beads 50 and/or 51 and/or 52 cannot pass through a window. In some applications, the width of window 62 is less than the diameter of beads 50 and/or 51 and/or 52. Windows 62 are covered by a membrane 32 stretched over the opening in a configuration to prevent the material inside from moving. (For some applications, all of tube 60 is covered by membrane 32.) There are three window cutouts portrayed in FIG. 4 (exploded Section A-A) by way of illustration and not limitation.

To facilitate diffusion of the analyte into the sampling region 26, windows 62 lie along the side of cylindrically-shaped perforated tube 60 in a plane that is parallel to the extension of optical fiber 10, i.e., on a lateral wall of perforated tube 60.

Perforated tube 60 is coupled to optical fiber 10 either mechanically or with a fast curing adhesive. In some applications, the adhesive is UV-cured.

A ring, in some applications, an o-ring (not shown), coupled to perforated tube 60, is configured to seal fluid passage at the interface between perforated tube 60 and optical fiber 10.

In some applications, sampling region 26 has a diameter of between 0.05 and 0.5 mm, and a height between 0.1 and 2 mm.

Figure 5:
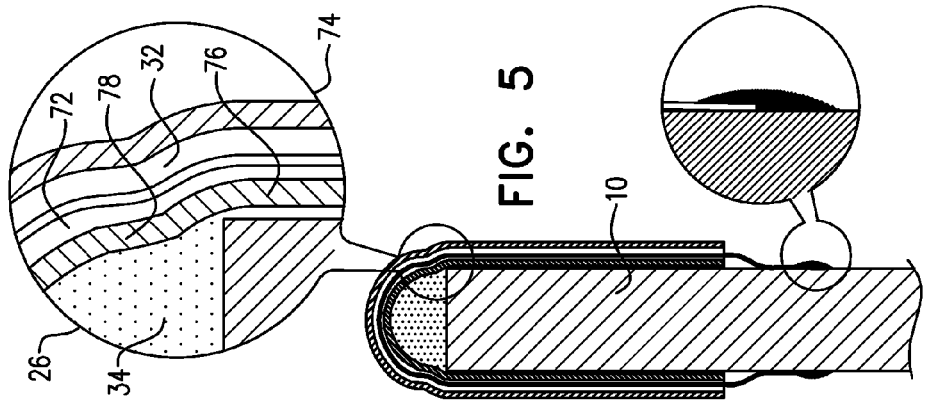

FIG. 5 is a schematic illustration of sampling region 26, as described hereinabove with reference to FIGS. 2A-B, with the exception that membrane 32 is sandwiched between a perforated tube 72 and a perforated tube 74.

Diffusive membrane 32 is at least in part in a plane perpendicular to the extension of optical fiber 10, and takes the general shape of a partial spherical surface at the end of optical fiber 10. This configuration provides a relatively large ratio of diffusive surface to volume in sampling region 26, the ratio growing as the diameter of optical fiber 10 becomes smaller. For example, in the case that the sampling region is a hemisphere, the ratio between the area of the membrane and the volume of sampling region 26 is 6/D, where D is the diameter of optical fiber 10. In some applications, in which the sampling region 26 has a diameter of between 0.05 and 0.5 mm, the surface to volume ratio will accordingly be between 120 and 12 $mm^{-1}$.

Typically, membrane 32 and tubes 72 and 74 are press fitted to create a hemispherical sampling region 26, however, other shapes may also be used, including tubular and other shapes; sampling region 26 is a hemisphere, by way of illustration and not limitation. Tubes 72 and 74 are typically stainless steel, but could be an alternative material as well. Perforated tube 72 is typically coupled to optical fiber 10 by glue, although other methods of coupling the tube to the fiber can also be implemented.

Membrane 32 is typically attached by glue to both tubes 72 and 74 within the area that perforated tube 72 coincides with the length of optical fiber. The glue is configured to prevent fluid passage into sampling region 26 other than that which passes through membrane 32. In other applications, other materials, in addition to, or instead of glue, may also be used.

Sampling region 26 typically comprises material 34 (which is typically optically-transparent and glucose-permeable). Perforated tube 72 has a larger-diameter portion 76 and a smaller-diameter portion 78. Portion 76 allows the optical fiber to slide into place, and portion 78 prevents the optical fiber from advancing into the area housing material 34 (which can house either cells (not shown), sensor proteins (not shown) or beads 50 and/or 51 and/or 52, as shown hereinabove with reference to FIG. 2B).

In some applications, sampling region 26 has a diameter of between 0.05 and 0.5 mm and height between 0.05 and 0.5 mm.

Figure 6:
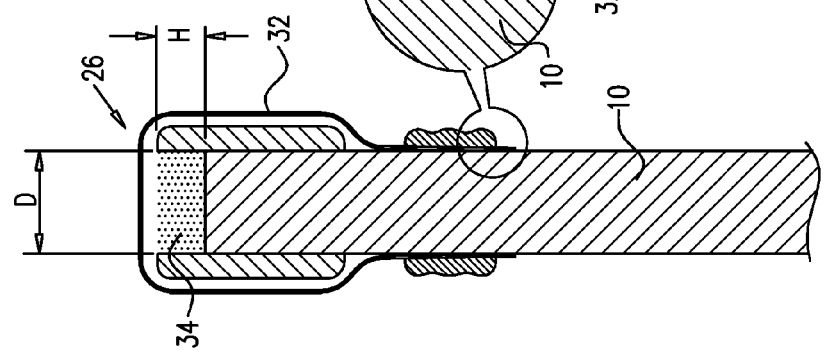

FIG. 6 is a schematic illustration of sampling region 26, as described hereinabove with reference to FIGS. 2A-B, with the exception that a ring 80 is used to seal membrane 32 to optical fiber 10, and that the diffusive surface of membrane 32 is in a plane perpendicular to the extension of optical fiber 10.

In some applications, sampling region 26 is configured to provide a short diffusion distance for light from optical fiber 10. For example, the diameter D of sampling region 26 is typically at least 1.5, or between 1.5 and 2, e.g., 2 times greater than the height H of the sampling region. Typically, the distal end of the sampling region is less than 0.6 mm, e.g., less than 0.4 mm from the distal end of fiber 10. This configuration provides a large ratio of diffusive surface to volume of sample region 26, because the height of sample region 26 is typically small relative to its diameter.

In this application of the invention, sampling region 26 typically but not necessarily contains beads 50 and/or 51 and/or 52 (described hereinabove; not shown in FIG. 6). Material 34, housed within membrane 32, is typically optically-transparent and glucose-permeable material, as described hereinabove. Material 34 can house either cells that make sensor proteins, or sensor proteins that are not generated by cells within sampling region 26, as described hereinabove.

Figure 7:
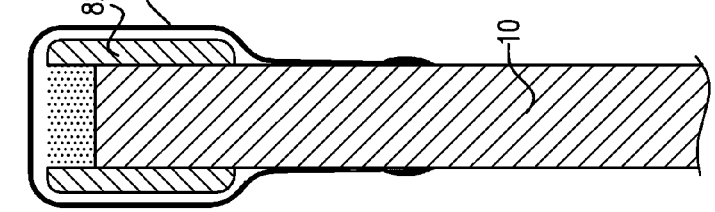

FIG. 7 is a schematic illustration of sampling region 26, as described hereinabove with reference to FIG. 6, with the exception that glue is used to seal membrane 32 to optical fiber 10. A tube 82 is sealed around optical fiber 10, and typically, but not necessarily, does not have perforations or windows along its wall.

The diffusive surface of membrane 32 is in a plane perpendicular to the extension of optical fiber 10. In some applications, sampling region 26 is configured to provide a short diffusion distance for light from optical fiber 10. For example, the diameter D of sampling region 26 is typically at least 1.5, or between 1.5 and 2, e.g., 2 times greater than the height H of the sampling region. Typically, the distal end of the sampling region is less than 0.6 mm, e.g., less than 0.4 mm from the distal end of fiber 10. This configuration provides a large ratio of diffusive surface to volume of sample region 26, because the height of sample region 26 is typically small relative to its diameter.

FIG. 8 is a schematic illustration of sampling region 26. Sampling region 26 is depicted without beads 50 and/or 51 and/or 52 for illustrative purposes only. In some applications, sampling region 26 may have beads 50 and/or 51 and/or 52. The volume of sampling region 26 is defined by a first thin-walled tube 90 having a distal end 92 and a proximal end 94. A second tube 96 has a distal end 98 and a proximal end 100. The wall thickness of tubes 90 and 96 typically ranges from 0.01 mm to 0.1 mm, e.g., 0.03 mm. Membrane 32 is stretched over the distal end of tube 96 and tube 90 is slid over tube 96 from above, tightly fitting around tube 96, and stretching membrane 32, in effect creating a double-walled cup structure with a proximal end and a distal end. The proximal end of the cup is open (and facing downward, in the figure toward optical fiber 10). The distal end of the cup is defined by membrane 32.

In some applications, sealing and/or gluing material is applied into the area between the double walls defined by tubes 90 and 96. The glue is typically applied far enough from the distal end of sampling region 26 in order to avoid blocking membrane 32 by glue infiltration. The sealing and/or gluing material is configured to seal the area between the double walls of the apparatus, defined by tubes 90 and 96, and to prevent fluid passage through the double-walled area into sampling region 26. Typically, this application of the invention is configured such that there is no fluid passage into sampling region 26 through the double-walled area, as defined by tubes 90 and 96, nor between tube 96 and optical fiber 10. This application of the invention is typically configured to allow fluid passage into and out of sampling region 26 only through membrane 32 at the distal end of the cup described hereinabove.

In some applications, membrane 32 is relatively rigid and is configured to facilitate diffusion of the measured analyte as well as other factors from the subject that support cell viability, e.g., nutrients and/or oxygen, into sampling region 26.

The diffusive surface of membrane 32 is in a plane perpendicular to the extension of optical fiber 10. In some applications, sampling region 26 is configured to provide a short diffusion distance for light from optical fiber 10. For example, the diameter D of sampling region 26 is typically at least 1.5, or between 1.5 and 2, e.g., 2 times greater than the height H of the sampling region. Typically, the distal end of the sampling region is less than 0.6 mm, e.g., less than 0.4 mm from the distal end of fiber 10. This configuration provides a large ratio of diffusive surface to volume of sample region 26, because the height of sample region 26 is typically small relative to its diameter.

Optical fiber 10 fits into proximal end 100 of second tube 96. A ring 104 is glued or otherwise attached to the optical fiber and contacts proximal end 100 of second tube 96. As appropriate: (a) proximal end 94 of first tube 90 may surround ring 104, (b) proximal end 94 of tube 90 may contact ring 104 without surrounding the ring, or (c) proximal end 94 of tube 90 may not contact ring 104. In any case, tube 90, tube 96, and/or ring 104 operate together to seal in sampling region 26 and to define the height of sampling region 26. The sampling region typically comprises an optically-transparent and glucose-permeable material 34 (material 34 is shown in FIG. 6, for example). Material 34 can house cells that generate sensor proteins, sensor proteins dispersed in material 34, or beads 50 and/or 51 and/or 52 (as described hereinabove with reference to FIG. 2B).

A sealing and/or gluing material (not shown) is applied between tube 90 and tube 96. The sealing and/or gluing material is configured to keep tubes 90 and 96 together and to prevent fluids from outside the device accessing sampling region 26.

In some applications, second tube 96 is sealed to optical fiber 10 by either glue and/or a mechanical ring (not shown) that presses the cup against optical fiber 10.

In some applications, ring 104 is made of the same material as tube 96. Further, tube 90 is, in some applications, longer at distal end 92, than tube 96 such that when ring 104 stops the further progression of tube 96 within tube 90, tube 90 covers (fully or partially) ring 104, creating a gluing surface.

Although FIG. 8 shows membrane 32 extending a certain distance along the outer surface of second tube 96, it is noted that the scope of the present invention includes having the membrane extend further (proximally), or not as far along the outer surface of second tube 96.

In some applications, a soft-material ring (not shown) that fits between second tube 96 and optical fiber 10 is configured to provide sealing therebetween.

In further applications, the soft-material ring, is applied between the proximal portion of tube 90 and ring 104.

In some applications, sampling region 26 is configured to provide a short diffusion distance for light from optical fiber 10, since the distal end of sampling region 26 is within 0.5 or 0.3 mm of the distal end of optical fiber 10.

For applications in which bead 50 and/or 51 and/or 52 is included in sampling region 26 (not shown), the sampling region is configured to tightly fit the bead in place.

In some applications, sampling region 26 is configured to provide good optical coupling between bead 50 and/or bead 52 (not shown) and optical fiber 10. Typically, direct contact between bead 50 and/or 51 and/or 52 and the distal end of optical fiber 10 are maximized to the extent that bead 50 and/or 51 and/or 52 do not break from that contact. This is typically achieved by exerting slight pressure on beads 50 and/or 51 and/or 52 by membrane 32, and/or first thin-walled tube 90, and/or second tube 96.

In some applications, when the height of sample region 26 is slightly smaller than the diameter of bead 50 and/or 51 and/or 52, the bead is squeezed toward optical fiber 10 as well as toward membrane 32, yielding a situation wherein optical coupling is improved and a shorter diffusion distance is achieved.

In some applications, sampling region 26 has a diameter of between 0.05 and 0.5 mm.

Figure 9:
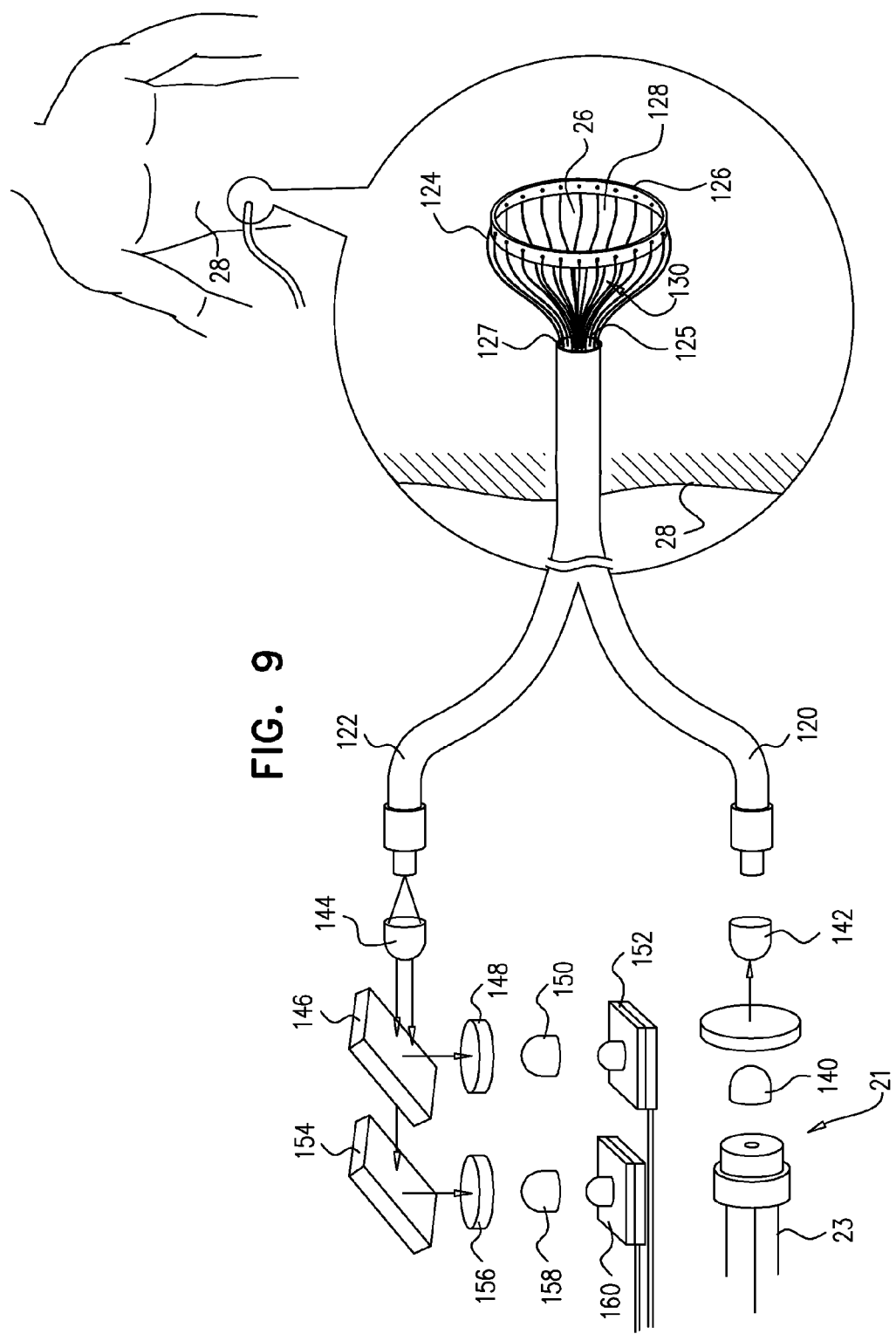
FIGS. 9-14 are further schematic illustrations of subcutaneously-implanted membrane-covered sensors and external devices, in accordance with some applications of the present invention.

FIG. 9 is a schematic illustration showing FRET fluorescence excitation and subsequent detection of analyte occurring in a substantially flat sampling region 26, in accordance with some applications of the present invention. Optical fiber bundles 122 and 120 convey light back and forth respectively to sampling region 26. Sampling region 26 lies inside ring 124, ring 124 having a diameter of 1 to 10 mm, e.g., 8 mm. A set of radial holes 126 (for example, 10 to 50 radial holes, e.g., 14 holes) through the wall of ring 124 serves for fixing the ends of optical fibers 125 and 127, shown by way of example and not limitation, that are splits of optical bundles 120 and 122, respectively.

As shown in FIG. 9, sampling region 26 has two large exposed flat surfaces thereof, i.e., the upper 128 and lower 130 large exposed surfaces of the sampling region. These large exposed surfaces provide a large interface area of sampling region 26 with the surroundings of the device, thereby supporting better exchange of material (e.g., glucose). Typically, a supportive element is present, e.g., selective membrane 32 (not shown), at the interface between sampling region 26 and the surrounding environment. This element typically serves as a means for keeping or fixing fluorescent material (not shown) in place within sampling region 26, as well as for selecting the fluid components that can be exchanged with the surrounding environment. For example, in the case of an implantable device, membrane 32 allows the permeation of analytes of interest into the sample region 26, while restricting passage therethrough of components from within sampling region 26 into the subject's body which could, among other things, potentially activate the immune system. Additionally, membrane 32 inhibits agents of the immune system from entering sampling region 26.

Appropriate reflective and scattering optical properties of the fluorescent material (not shown) in sample region 26 and/or of the supportive element, e.g. membrane 32 (not shown) contribute to enhancing both the effectiveness of the fluorescence exciting light, as well as directing a larger portion of the fluorescently-emitted light towards extracorporeal detection system 22.

Thus, typically, sampling region 26 houses a fluorescent material (not shown), which is excited by light, having a first wavelength, which is emitted by light source 23 of extracorporeal detection system 22, and, responsively to the excitation of the FRET molecules (not shown) emits light in wavelengths that are higher than the excitation wavelength. Typically, the emission parameters of the light emitted from the FRET molecules are proportionately affected in response to an analyte in sampling region 26. Part or all of these parameters, e.g., the intensity of the fluorescent emitted light in selected wavelength ranges, are measured by electro-optical unit 21 in extracorporeal detection system 22. Thus, concentrations of the analyte in sampling region 26 are measured responsively to the changes in emission parameters of the light emitted by the FRET molecules.

More specifically, in FIG. 9, excitation light that is emitted by light source 23 (e.g., here a laser diode shown by way of illustration but not limitation) is typically collimated by a first lens 140 and then focused by a second lens 142 into first, proximal, ends of optical fibers assembled in optical fiber bundle 120. The distance between second lens 142 and optical fiber bundle 120 is typically determined by optimizing for a combination between light spot size and sharpness. At the second, distal end of optical fiber bundle 120, optical fibers 125 are typically spread evenly along the perimeter of ring 124 and deliver the excitation light into sampling region 26, where the light excites a fluorescent material (not shown) disposed therein. Fluorescence emitted light is then collected by the first, distal, ends of optical fibers 127 that are assembled in optical fiber bundle 122, to deliver the fluorescent light for detection by electro-optical unit 21 in extracorporeal detection system 22.

The fluorescent light that is received at the second, proximal, ends of optical fibers 127, in optical fiber bundle 122, is in some applications, collimated by lens 144 and split into two spectral bands by dichroic beam splitter 146. One spectral band is reflected by beam splitter 146, and the other spectral band is transmitted through the beam splitter. The reflected light beam is filtered by a first narrow band filter 148, which filters a first fluorescent emission spectral band, and is afterwards focused by a lens 150 onto a light detector 152 (e.g., a photodiode), which measures the intensity of the first fluorescent emission spectral band. The distance between lens 150 and photodiode 152 is typically the focal length of the lens. The light transmitted through beam splitter 146 is reflected by a mirror 154 through a second narrow band filter 156, which filters a second fluorescent emission spectral band, and is afterwards focused by lens 158 onto light detector 160 (e.g., a photo diode), which measures the intensity of the second fluorescent emission spectral band. The distance between lens 158 and photodiode 160 is typically the focal length of the lens. Mirror 154 is not mandatory from a functional perspective, rather it serves primarily for making the structure of extracorporeal detection system 22 more compact. Alternatively, mirror 154 could be replaced by a second beam splitter (configuration not shown) that would add a filtering stage to the filtering of the fluorescent emitted light by reflecting a selected range of wavelengths towards detector 160, and transmitting away wavelengths that are not of interest. Such a process increases the signal to noise ratio of the system.

The configuration of sample region as shown in FIG. 9 provides a large interface area of sampling region 26 with the surrounding environment. Accordingly, it has the advantage of minimizing the average distance between the surface of the sample region and any point inside it, shortening, for example, the diffusion distance of a measured analyte from the outside environment into the sampling region, and shortening, accordingly, the response time of the device. In addition, the application of the invention shown in FIG. 9 provides simplicity, compactness, and a slim structure that improves the ease of implantation.

Figure 10:
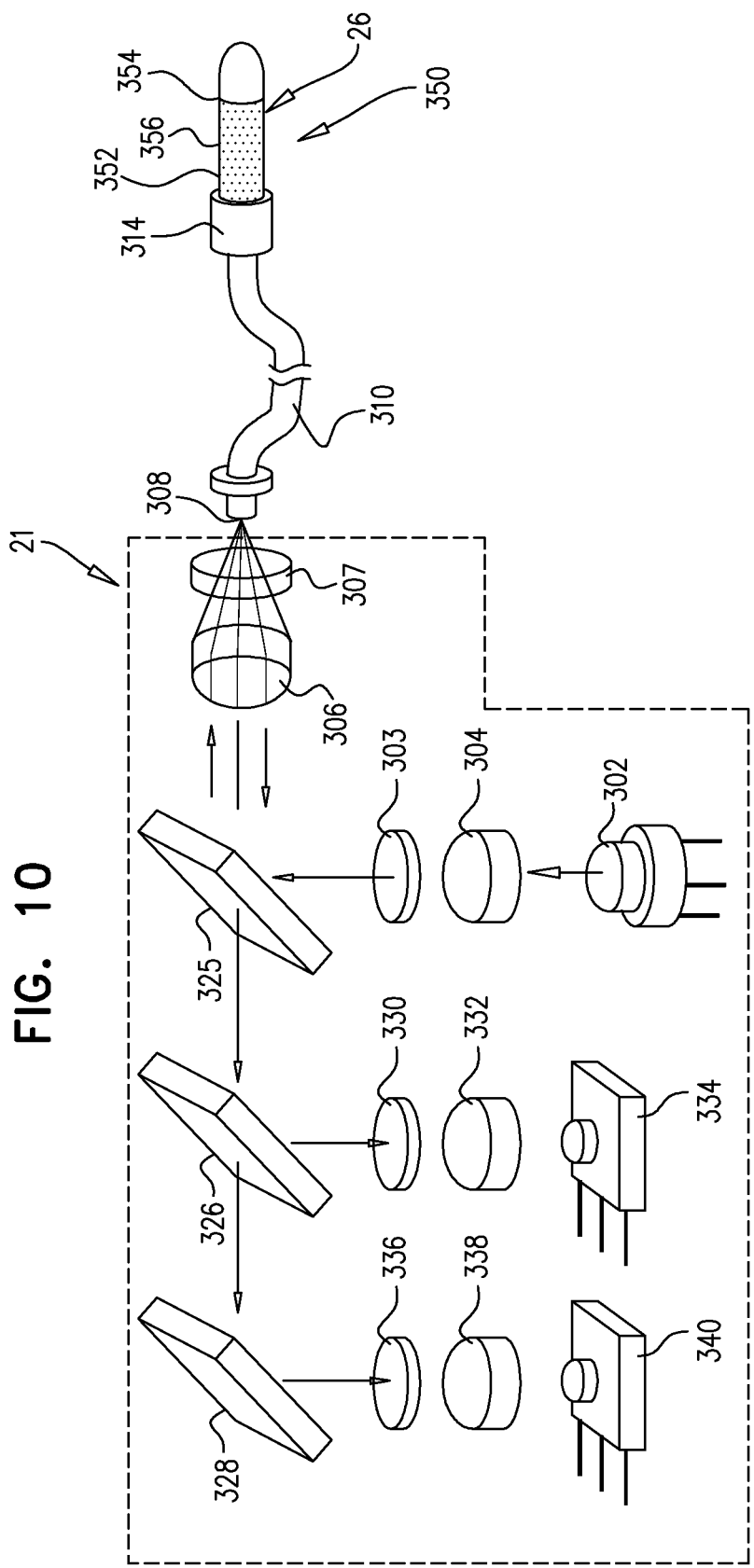

FIG. 10 shows an application of an optical sensor device in which a single optical fiber transmits light back and forth from an electro-optical unit 21 to sample region 350, in accordance with an application of the present invention. For fluorescence detection, excitation light that is produced by electro-optical unit 21 is transmitted to the fluorescent material (not shown) in sample region 350 by an optical fiber 310. Fluorescent light that is consequently emitted by the fluorescent material is transmitted in the opposite direction from sample region 350 to the electro-optical unit 21 through the same optical fiber 310.

More specifically, in the application shown in FIG. 10, excitation light that is emitted by light source 302, e.g., a laser diode, is collimated by lens 304. A dichroic beam-splitter 325 reflects the light from light source 302 towards the proximal end 308 of optical fiber 310 and passes undesired parts of the emission spectrum of light source 302. Lens 306 focuses the collimated beam into proximal end 308 of optical fiber 310, while an additional optical window 307 may serve as a dust protection unit. Optical fiber 310 delivers the illumination light to sample region 350 at its second, distal end 314, where it excites a fluorescent material (not shown) that is disposed therein. Fluorescence emitted light is then collected by distal end 314 of optical fiber 310 and delivered back into electro-optical unit 21. Electro-optical unit 21 comprises a lens 306, which collimates the fluorescent light that is transmitted through first dichroic beam splitter 325 to a second beam splitter 326, where it is split into two spectral bands of interest. A first spectral band is reflected towards a first light detector 334, and a second spectral band is transmitted towards mirror 328. Mirror 328 is in some instances a folding mirror configured to change the propagation direction of the light beam. The first reflected light beam is filtered by a first narrow band filter 330, which passes the first fluorescent emission spectral band, and is afterwards focused by a lens 332 onto light detector 334, e.g., a photo diode, which measures the intensity of the first fluorescent emission spectral band. The second transmitted light beam is reflected by mirror 328 through a second narrow band filter 336, which passes a second fluorescent emission spectral band. The filtered light is afterwards focused by a lens 338 onto a second light detector 340, e.g., a photo diode, which measures the intensity of the second fluorescent emission spectral band. Mirror 328 serves primarily for making the structure of electro-optical unit 21 compact. Alternatively, mirror 328 may be replaced by a third beam splitter, which adds a filtering stage to the filtering of the fluorescent emitted light, by reflecting a selected range of wavelengths of interest towards detector 340 and by transmitting away wavelengths that are not of interest. Such a process may in some applications increase the signal to noise ratio of the system.

The use of a laser as light source 302, e.g., a laser diode shown for illustration but not limitation, has the typical advantage of comprising a relatively small light emitting element which produces light in a relatively narrow spectral band. The small size of the light emitting element makes it suitable for efficient transmittance of light power into optical fiber 310, by suitable focusing optics. The narrow spectral band is suitable for fluorescence applications, where the separation between the excitation spectrum and the fluorescence emission spectra is utilized. However, the addition of a narrow band filter 303 to the above described embodiment would allow the application of light sources with a spectral emission band that is broader than the laser band. Such light sources, e.g., LED's, for some applications have relative advantages of availability, stability, ease of operation, cost, and other considerations.

Typically, sample region 350 houses a fluorescent material, which is excited by light having a first wavelength, which is produced by light source 302 of electro-optical unit 21, and, responsively to the excitation via light source 302, emits light in wavelengths that are higher than the excitation wavelength. The intensity of the fluorescence emitted light in selected wavelength ranges is measured by electro-optical unit 21. Thus, the concentration of the analyte in region 350 is measured responsively to changes in emission parameters of the light emitted by the fluorescent material.

As shown in FIG. 10, sampling region 350, is provided having distal end 314 of optical fiber 310 connected to a rigid skeletal structure, e.g., a perforated tube 352, which positions the fluorescent material at the end of optical fiber 310. In some applications, improved optical performance is achieved by having the fluorescent material covering the entire cross section of optical fiber 310. In some applications, sampling region 350 is similar or identical to sampling regions 26 described hereinabove with reference to FIGS. 2-8.

In this exemplary application, the fluorescent material is encapsulated in transparent beads (not shown) of a size that typically does not allow the beads to pass through the holes of perforated tube 352. Typically, the density of the holes in perforated tube 352 can be as high as the desired rigidity of perforated tube 352 permits, and the wall thickness of perforated tube 352 is typically accordingly as thin as the desired rigidity of perforated tube 352 permits. The diffusion of the analyte increases between the fluorescent material and the surrounding environment, with a higher perforation density and a thinner wall.

A stopper 354, e.g., a silicone plug, closes perforated tube 352 from the side opposite to distal end 314 of optical fiber 310. In some applications, the stopper maintains the fluorescent material in place.

A selective membrane 356, e.g., a perforated polyvinylidene difluoride (PVDF) membrane shaped as a tube, typically seals the entire sample region 350. It typically serves to select fluid components that can be exchanged with the surrounding environment. The membrane allows the permeation of analytes of interest, while restricting passage therethrough of components from within region 350 into the body which could potentially activate the immune system. Additionally, the membrane restricts passage therethrough of agents of the immune system from entering the sample region. Appropriate reflective and scattering optical properties of perforated tube 352 and membrane 356 contribute to enhancing both the effectiveness of the fluorescence exciting light as well as directing a larger portion of the fluorescent emitted light towards electro-optical unit 21.

Figure 11:
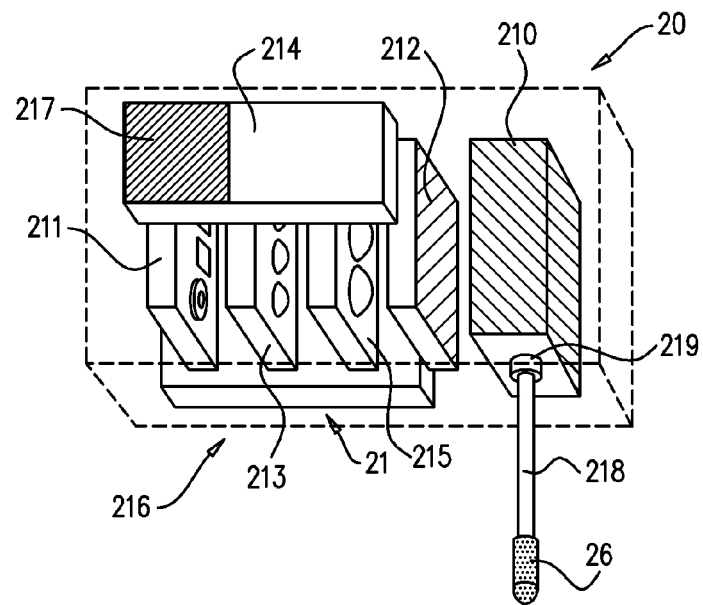

FIG. 11 is a schematic illustration of detection system 22 for coupling with implantable sampling region 26 of measuring device 20, in accordance with an application of the present invention. Detection system 22 comprises electro-optical unit 21, which typically operates as described hereinabove with reference to FIG. 10. Electro-optical unit 21 comprises a filter-cube array 212 having a plurality of filters that are aligned as shown in FIG. 11, and which operate as described with reference to FIG. 10.

Typically, the individual electronic components of electro-optical unit 21 are board-mounted on an electronic card. A light source and detection unit 211 comprises one or more light sources and one or more detectors (typically one light source and two detectors), which operate as described with reference to FIG. 10. A pinhole unit 213 is shaped to define one or more pinholes that are aligned with the light source and/or with the one or more detectors of unit 211. The alignment between pinhole unit 213 and light source and detection unit 211 is, in some applications, configured to prevent crosstalk between distinct components of electro-optical unit 21. In some applications, the pinholes in pinhole unit 213 narrow the light beams approaching the detectors on light source and detection unit 211. In further applications, pinholes in pinhole unit 213 are configured to narrow the light beams emanating from the light source, so that light enters filter-cube array 212 (in some applications comprising interference filters) at an angle perpendicular to the face of array 212. A lens unit 215 comprises one or more lenses which operate as described with reference to FIG. 10. A beam splitter unit 210 comprises one or more dichroic beam splitters, which operate as described with reference to FIG. 10.

Spaces depicted between the units in measuring device 20 are for illustrative purposes; in some applications, two or more of these units (e.g., light source and detection unit 211, pinhole unit 213, lens unit 215, beam splitter unit 210, and filter-cube array 212) are in contact with each other.

Measuring device 20 typically has a port for a connector 219. Connector 219 is configured to reversibly couple electro-optical unit 21 with optical fiber 218 (or a light guide, not shown), and implantable sampling region 26, placing the sampling region in optical communication with electro-optical unit 21.

For some applications, the measuring device comprises a transceiver 217, an antenna 214, and an extracorporeal detection system 216. Typically, extracorporeal detection system 216 is similar to extracorporeal detection system 22 described hereinabove with reference to FIG. 1B. (In some applications, the systems are identical.) In some applications, transceiver 217 and antenna 214 are employed to transmit and receive data related to analyte content in sampling region 26. In some applications, measuring device 20 and sampling region 26 are both configured to be implantable within the body of the subject. In some applications, detection system 22 of measuring device 20 is configured to be coupled to the body of the subject extracorporeally.

Figure 12:
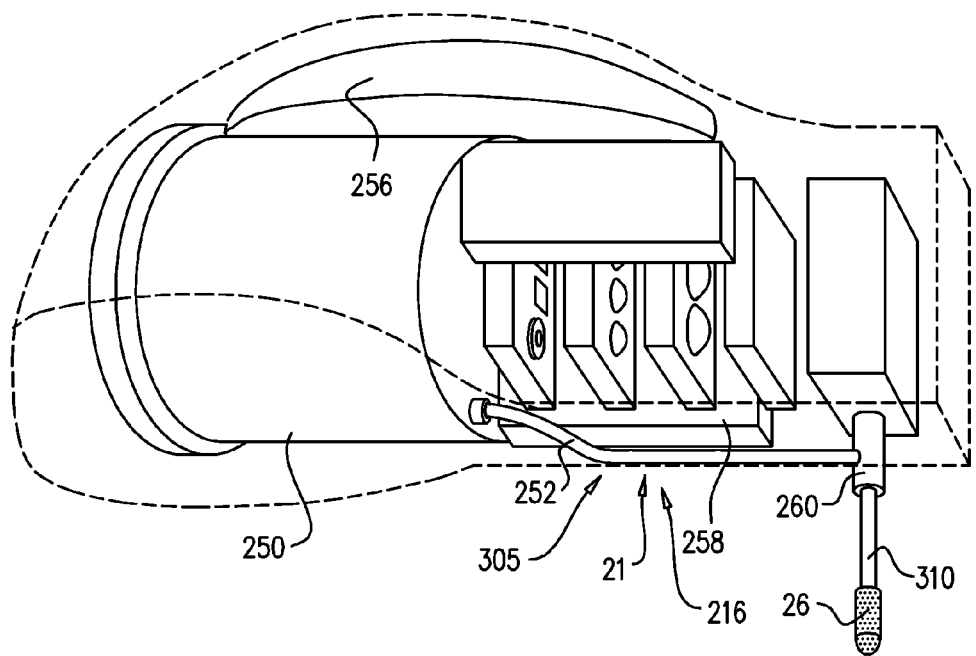

FIG. 12 is a schematic illustration of measuring device 20, in accordance with another application of the present invention. Extracorporeal detection system 216 of measuring device 20 is generally similar to electro-optical unit 21 (FIGS. 10-11), except with differences as noted.

Further, extracorporeal detection system 216 is typically similar to extracorporeal detection system 22 described hereinabove with reference to FIG. 1B. (In some applications the systems are identical.) Measuring device 20 is coupled to a replaceable insulin reservoir 250. Reservoir 250 is in communication with an activation unit (not shown) that turns on a pump mechanism (not shown), which is powered by a replaceable pump battery 256. The pump mechanism pumps insulin from reservoir 250, through an insulin tube 258, and out of measuring device 20, through an insulin dispenser 260.

Insulin dispenser 260 extends out of measuring device 20, and is typically capable of being implanted into the subject. Typically, the insulin concentrations are calibrated for the patient prior to implantation. In some applications, more than one insulin reservoir (not shown) is provided, each having a different respective concentration of insulin (of another different property). The desired insulin is administered based on sensing, time of day, or another parameter. Insulin from insulin tube 258 typically does not significantly affect the glucose readings derived from sampling region 26. In some applications, this is the case because the area to which insulin dispenser 260 dispenses insulin into the body of the subject is sufficiently separated from sampling region 26, e.g., 2-5 mm. In addition, with the sensing of glucose levels taking place only on one end of inserted optical fiber 310, i.e., at sampling region 26, and not all along the optical fiber 310 there is generally no material effect on the values of the analyte being sampled in sampling region 26.

For some applications, automatic detector calibration is provided using insulin reservoir 250, or, alternatively, another dedicated reservoir (not shown) which stores a glucose solution of known concentration. Upon entering an automatic calibration mode, the glucose solution is injected into sample region 26, and consecutive readings of the detection unit are calibrated to the known glucose concentration.

It is noted that the scope of the present invention includes replacing the extracorporeal detection system described with regard to FIG. 12 with an intracorporeal detection system. In such a case, replaceable insulin reservoir 250 typically remains extracorporeal.

Figure 13:
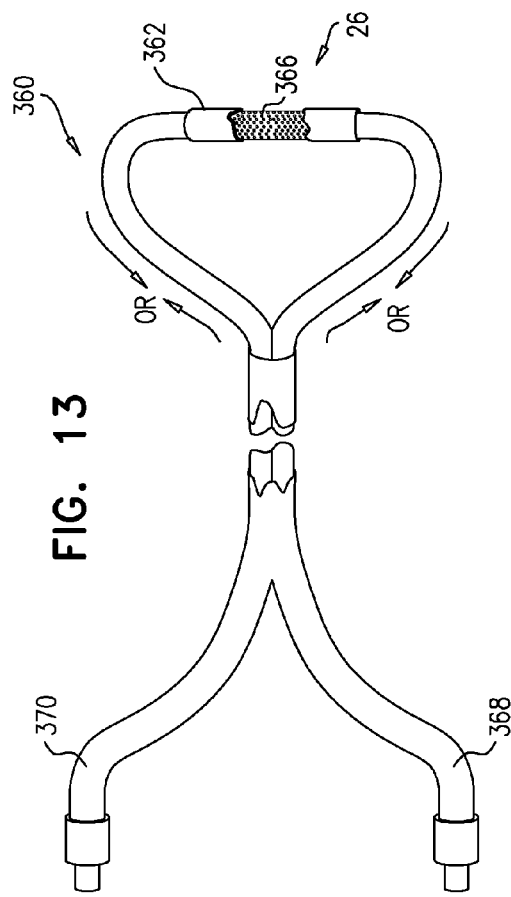
Figure 14:
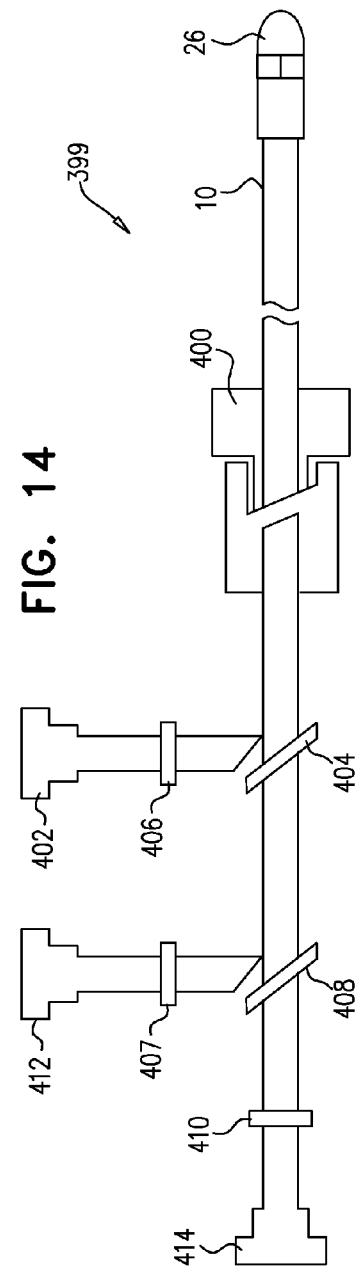

FIG. 13 is a schematic illustration of light transmission apparatus, in which a separate set of fibers 370 are dedicated to transmitting light from a light source (not shown) toward sampling region 26, which is surrounded by a membrane 362 (shown here cut-away for illustrative purposes only) and a perforated tube 366. A separate set of fibers 368 carry light from sampling region 26 toward the extracorporeal detection system (not shown), e.g., electro-optic unit 21 of FIG. 9. For some applications, fibers 370 and/or fibers 368 carry light both to and from sampling region FIG. 14 is a schematic illustration, showing a device 399, as an alternative to the free space optics depicted in some of the prior figures, in accordance with an application of the present invention. In applying all-fiber optics, device 399 typically does not use lenses and allows for smaller optics, facilitating easy implantation of device 399. Sample region 26 is coupled to optical fiber 10. Optical fiber 10 is coupled to a fiber connector 400. Excitation light produced by a laser diode 402, or an alternative light source, travels through a fiber-coupled narrow-band filter 406 and is reflected by a fiber-coupled dichroic beam splitter 404 and travels through optical fiber 10 toward sample region 26. Fluorescent light from sample region 26 travels back via optical fiber 10, passes through fiber-coupled dichroic beam splitter 404 toward a second fiber-coupled beam splitter 408, splitting the emission into two wavelength bands. One wavelength is reflected by beam splitter 408 through a narrow band filter 407, exciting a fiber-coupled photodiode 412. A second wavelength passes through beam splitter 408, through a second narrow band filter 410, exciting a second filter-coupled photodiode 414.

In some configurations, dichroic beam splitters 404 and 408 and narrow band filters 406, 407, and 410 utilize fiber couplers with embedded thin glass filters, or direct dichroic coating on polished fiber ends. This second configuration is typically when the optical fiber material comprises glass (e.g., quartz).

In some applications, device 399 is embedded in or mounted on an electronic card (not shown) and includes measuring device 20 described with reference to FIG. 1B. For such applications, measuring device 20 comprises an extracorporeal detection system 22 which, in addition to the detection unit 21 also comprises a power source 24 and a control unit 25, in accordance with some applications of the present invention.

It is noted that the scope of the present invention includes replacing the extracorporeal detection system described with regard to FIG. 14 with an intracorporeal detection system, such that measuring device 20, including extracorporeal detection system 22, is entirely implantable within the subject.

Device 399 is, in some applications, configured to be a fully implantable device, which transmits measured data to an external transceiver (not shown), which, in turn, includes control and display units (not shown).

Typically, power source 24 is configured to run continuously in a duty cycle that consists of repeated sleeping modes separated by short bursts of measurement states. In some applications, power source 24 is configured to operate on demand. In other applications, power source 24 operates continuously. In some applications, power source 24 is charged by an extracorporeal device (not shown).

Typically, when device 399 is implanted in the subject, sample region 26 is mounted directly on the surface of the device.

Figure 15:
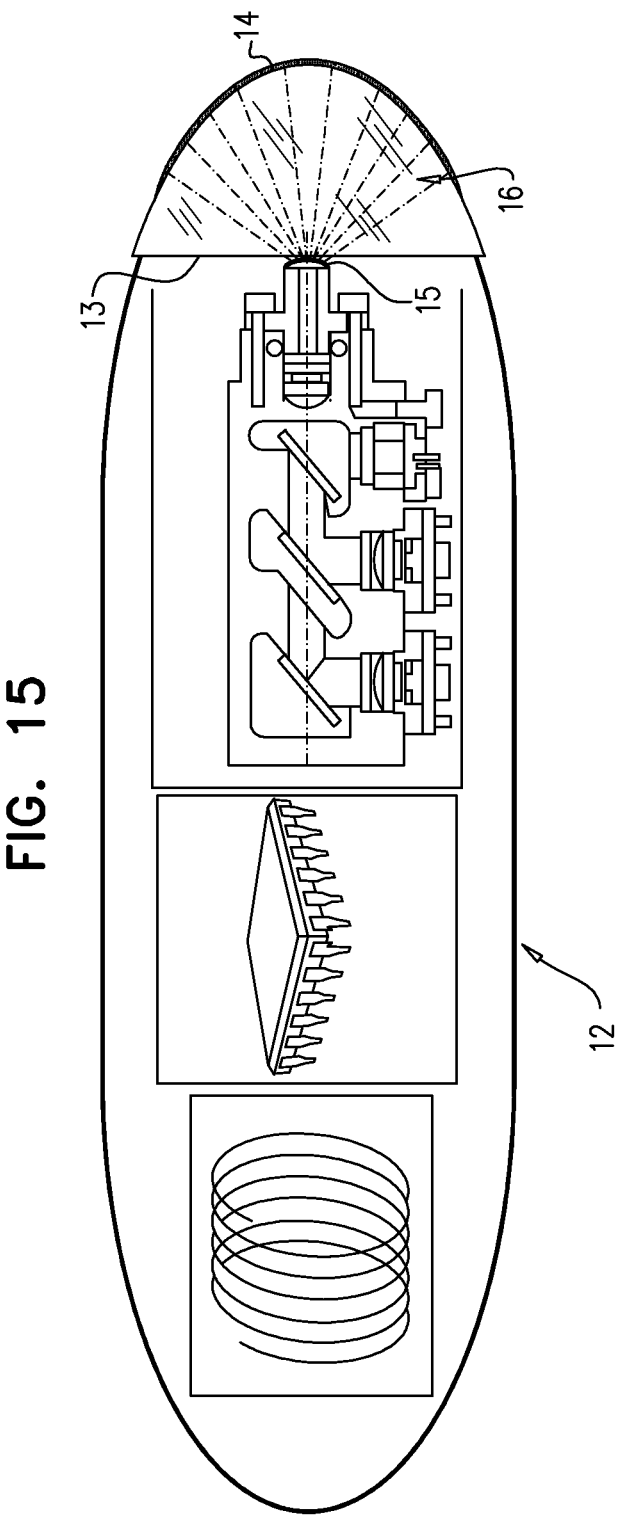
FIG. 15 is a schematic illustration of a subcutaneously-implanted injectable device, coupled, without an optical fiber, to a sampling region, in accordance with some applications of the present invention.

Reference is now made to FIG. 15, which is a schematic illustration of an injectable device 12, in accordance with some applications of the present invention. Injectable device 12 is generally similar to injectable device 17 in FIG. 1A, except with differences as noted.

A selectively-permeable membrane 14 is typically coupled to one end of injectable device 12. Selectively-permeable membrane 14 typically is configured to restrict passage therethrough of substances, e.g., cells, which could potentially interfere with the measuring of an analyte. Typically, selectively-permeable membrane 14 is secured to injectable device 12 via a ring 13. In some applications, selectively-permeable membrane 14 is coupled to injectable device 17 via glue or another sealing material known in the art.

The area enclosed by selectively-permeable membrane 14 and injectable device 12 is configured to be a sampling region 16 for an analyte, typically glucose. Sampling region 16 is generally similar to sampling regions described hereinabove with reference to FIGS. 1-14, except with differences as noted.

A lens 15 is typically coupled to electro-optical unit 21, and is configured to direct light entering and exiting electro-optical unit 21, to and from sampling region 16.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus for detecting an analyte, configured to be implanted in a body of a subject, the apparatus comprising:
   an optical fiber having a distal portion;
   a membrane permeable to the analyte, the membrane coupled to the distal portion of the fiber and surrounding a sampling region at least in part, by being fitted over the distal portion of the fiber, the sampling region being entirely distal to the fiber and comprising a glucose-permeable material; and
   a perforated tube surrounding the sampling region,
   wherein the membrane surrounds the perforated tube.

2. The apparatus according to claim 1, wherein the optical fiber comprises exactly one optical fiber.

3. The apparatus according to claim 1, wherein the membrane is attached to the distal portion of the fiber within 5 mm of a distal tip of the fiber.

4. The apparatus according to claim 1, wherein the membrane is attached to the distal portion of the optical fiber by glue.

5. The apparatus according to claim 1, wherein the distal portion of the optical fiber is disposed within the perforated tube.

6. The apparatus according to claim 1, wherein the perforated tube comprises a material selected from the group consisting of: metal and plastic.

7. The apparatus according to claim 1, wherein the sampling region has a shape selected from the group consisting of: cylindrical and hemispherical.

8. The apparatus according to claim 1, wherein the membrane is shaped to define a hole therein that is sealed, the sealed hole located at a distal end of the sampling region relative to the optical fiber.

9. The apparatus according to claim 1, further comprising a stopper inserted into a distal end of the perforated tube relative to the optical fiber.

10. The apparatus according to claim 1, further comprising:
    a light source configured to pass light through the optical fiber toward the sampling region; and
    a detection system, configured to receive fluorescent light, through the optical fiber, from the sampling region, and to analyze the fluorescent light in order to determine an indication of a level of the analyte in the body of the subject.

11. The apparatus according to claim 10, wherein the detection system is configured to facilitate administration of a substance to the subject, in response to the determined indication of the level of the analyte.

12. The apparatus according to claim 10, wherein the detection system is configured to determine the indication of the level of the analyte, while outside of the body of the subject.

13. The apparatus according to claim 10, wherein the detection system is configured to be implanted in the body of the subject, and to determine the indication of the level of the analyte, while inside the body of the subject.

14. The apparatus according to claim 1, wherein the sampling region comprises biological matter, which changes a state thereof in response to a concentration of the analyte in the subject.

15. The apparatus according to claim 14, wherein:
    the biological matter comprises a plurality of fluorescent proteins including a genetically-modified glucose receptor protein, and a cyan fluorescent protein (CFP) and a yellow fluorescent protein (YFP) coupled to the glucose receptor protein, and is configured such that:
    when a glucose molecule from the subject interacts with the genetically-modified glucose receptor protein, the glucose receptor protein changes conformation as a result, and the two fluorescent proteins are in close enough proximity to each other so that the CFP acts as an energy donor and the YFP acts as an energy acceptor in a Fluorescence Resonance Energy Transfer (FRET) signaling system that indicates a concentration of glucose through the emission of electromagnetic radiation.

16. The apparatus according to claim 15, wherein the biological matter comprises a plurality of cells, which produce the genetically-modified glucose receptor proteins.

17. The apparatus according to claim 14, further comprising one or more alginate beads encasing the biological matter.

18. The apparatus according to claim 17, wherein each bead has a diameter of 40 um to 150 um.

19. The apparatus according to claim 17, wherein each bead has a diameter of 150 um to 600 um.

20. The apparatus according to claim 17, wherein each bead has a diameter equal to 60% to 80% of an internal diameter of the perforated tube.

21. The apparatus according to claim 17, wherein each bead has a diameter equal to 80% to 120% of a diameter of the optical fiber.

22. The apparatus according to claim 17, wherein the one or more alginate beads comprise exactly two alginate beads.

23. The apparatus according to claim 17, wherein the one or more alginate beads comprise exactly three alginate beads.

\* \* \* \* \*